(12) United States Patent
Colgan

(10) Patent No.: US 8,962,530 B2
(45) Date of Patent: Feb. 24, 2015

(54) INFLAMMATORY BOWEL DISEASE THERAPIES

(75) Inventor: Sean P. Colgan, Denver, CO (US)

(73) Assignees: Regents of the University of Colorado, Denver, CO (US); The Brigham and Women's Hospital, Inc., Boston, MA (US)

( * ) Notice: Subject to any disclaimer, the term of this patent is extended or adjusted under 35 U.S.C. 154(b) by 743 days.

(21) Appl. No.: 12/666,438

(22) PCT Filed: Jun. 26, 2008

(86) PCT No.: PCT/US2008/007962
§ 371 (c)(1),
(2), (4) Date: Nov. 22, 2010

(87) PCT Pub. No.: WO2009/002533
PCT Pub. Date: Dec. 31, 2008

(65) Prior Publication Data
US 2011/0065771 A1 Mar. 17, 2011

Related U.S. Application Data

(60) Provisional application No. 60/946,537, filed on Jun. 27, 2007.

(51) Int. Cl.
*A61K 31/47* (2006.01)
*A61K 31/473* (2006.01)
*A61K 31/7088* (2006.01)

(52) U.S. Cl.
CPC .............. *A61K 31/47* (2013.01); *A61K 31/473* (2013.01); *A61K 31/7088* (2013.01)
USPC ....................................................... 504/307

(58) Field of Classification Search
CPC combination set(s) only.
See application file for complete search history.

(56) References Cited

U.S. PATENT DOCUMENTS

| | | | |
|---|---|---|---|
| 5,607,954 A | 3/1997 | Weidmann et al. |
| 5,610,172 A | 3/1997 | Weidmann et al. |
| 5,620,995 A | 4/1997 | Weidmann et al. |
| 5,620,996 A | 4/1997 | Weidmann et al. |
| 5,658,933 A | 8/1997 | Weidmann et al. |
| 5,719,164 A | 2/1998 | Weidmann et al. |
| 5,726,305 A | 3/1998 | Weidmann et al. |
| 6,020,350 A | 2/2000 | Weidmann et al. |
| 6,093,730 A | 7/2000 | Weidmann et al. |

(Continued)

FOREIGN PATENT DOCUMENTS

| | | |
|---|---|---|
| EP | 0 650 960 A1 | 5/1995 |
| EP | 0 650 961 A1 | 5/1995 |

(Continued)

OTHER PUBLICATIONS

Ulcerative Colitis: Inflammatory Bowel Diseases (IBD): Merck Manual Home Edition, Last full review/revision Aug. 2006 by David B. Sachar, MD; Aaron E. Walfish, MD.*

(Continued)

*Primary Examiner* — Marcos Sznaidman
*Assistant Examiner* — Rayna B Rodriguez
(74) *Attorney, Agent, or Firm* — Wolf, Greenfield & Sacks, P.C.

(57) ABSTRACT

The invention relates to methods of treating inflammatory bowel disease in a subject. Methods of promoting intestinal barrier function as well as related compositions are also provided.

20 Claims, 9 Drawing Sheets

(56) References Cited

U.S. PATENT DOCUMENTS

| | | | |
|---|---|---|---|
| 6,114,382 | A | 9/2000 | Moretti |
| 7,323,475 | B2 | 1/2008 | Arend et al. |
| 2005/0244915 | A1 | 11/2005 | Pugh et al. |
| 2006/0094676 | A1 | 5/2006 | Lahav et al. |
| 2006/0199836 | A1 | 9/2006 | Turtle et al. |
| 2006/0217416 | A1 | 9/2006 | Arend et al. |
| 2006/0276477 | A1 | 12/2006 | Klaus et al. |
| 2007/0042937 | A1 | 2/2007 | Klaus et al. |
| 2007/0048728 | A1* | 3/2007 | Ratcliffe et al. .............. 435/4 |
| 2007/0213335 | A1 | 9/2007 | Fitch et al. |
| 2007/0298104 | A1 | 12/2007 | Arend et al. |
| 2008/0004309 | A1 | 1/2008 | Deng et al. |

FOREIGN PATENT DOCUMENTS

| | | | |
|---|---|---|---|
| WO | WO 00/50390 | A1 | 8/2000 |
| WO | WO 03/049686 | A2 | 6/2003 |
| WO | WO 2006/094292 | A2 | 9/2006 |

OTHER PUBLICATIONS

Natarajan R, Salloum FN, Fisher BJ, Ownby ED, Kukreja RC and Fowler AA. Activation of hypoxia-inducible factor-1 via prolyl-4 hydoxylase-2 gene silencing attenuates acute inflammatory responses in postischemic myocardium. Am J Physiol Heart Circ Physiol, 2007; 293: H1571-H1580. First published Jun. 1, 2007; doi:10.1152/ajpheart.00291.2007.*
GENBANK Submission; NIH/NCBI, Accession No. AA046039; Wilson, May 11, 1997.
GENBANK Submission; NIH/NCBI, Accession No. AAA19321; Wax et al., Jun. 29, 1994.
GENBANK Submission; NIH/NCBI, Accession No. AAB41495; Tian et al., Jan. 28, 1997.
GENBANK Submission; NIH/NCBI, Accession No. AAB41496; Tian et al., Jan. 28, 1997.
GENBANK Submission; NIH/NCBI, Accession No. AAC72734; Gu et al., Nov. 6, 2001.
GENBANK Submission; NIH/NCBI, Accession No. AAD22668, Lamerdin et al., Jun. 17, 1999.
GENBANK Submission; NIH/NCBI, Accession No. AAD56365; Darby et al., Dec. 23, 1999.
GENBANK Submission; NIH/NCBI, Accession No. AAF52050; Adams et al., Dec. 11, 2009.
GENBANK Submission; NIH/NCBI, Accession No. AAG33965; Dupuy et al., Nov. 23, 2000.
GENBANK Submission; NIH/NCBI, Accession No. AAL27308; Mahon et al., Nov. 4, 2001.
GENBANK Submission; NIH/NCBI, Accession No. BAA20130; Ema et al., Dec. 27, 2005.
GENBANK Submission; NIH/NCBI, Accession No. BAA34234; Takahashi et al., Oct. 11, 2001.
GENBANK Submission; NIH/NCBI, Accession No. BAA78675; Hara et al., Sep. 16, 2006.
GENBANK Submission; NIH/NCBI, Accession No. CAA70701; Kietzmann et al.; Apr. 18, 2005.
GENBANK Submission; NIH/NCBI, Accession No. CAB96611; Kietzmann et al.; Apr. 15, 2005.
GENBANK Submission; NIH/NCBI, Accession No. CAB96612; Kietzmann et al.; Apr. 15, 2005.
GENBANK Submission; NIH/NCBI, Accession No. CAB96628; Kietzmann, Apr. 15, 2005.
GENBANK Submission; NIH/NCBI, Accession No. CAC42510; Taylor, Oct. 7, 2008.
GENBANK Submission; NIH/NCBI, Accession No. CAC42511; Taylor, Oct. 7, 2008.
GENBANK Submission; NIH/NCBI, Accession No. CAC42515; Taylor, Sep. 23, 2008.
GENBANK Submission; NIH/NCBI, Accession No. CAC42516; Taylor, Sep. 23, 2008.
GENBANK Submission; NIH/NCBI, Accession No. CAC42517; Taylor, Sep. 23, 2008.
GENBANK Submission; NIH/NCBI, Accession No. NC_00019.9; GI: 224589810; Grimwood et al., Jun. 10, 2009.
GENBANK Submission; NIH/NCBI, Accession No. NC_005118.2; GI: 62750819; Gibbs et al.. Apr. 5, 2010.
GENBANK Submission; NIH/NCBI, Accession No. NC_007864.1; GI: 109158192; Gibbs et al., Jun. 2, 2010.
GENBANK Submission; NIH/NCBI, Accession No. NP_060025; Pan et al., Mar. 11, 2007.
GENBANK Submission; NIH/NCBI, Accession No. NP_542770; Winning et al., Sep. 20, 2010.
GENBANK Submission; NIH/NCBI, Accession No. P59722; Duplan, Sep. 7, 2010.
GENBANK Submission; NIH/NCBI, Accession No. Q16665, Wang et al., Jun. 15, 2010.
GENBANK Submission; NIH/NCBI, Accession No. Q61221; Li et al., Sep. 7, 2010.
Boirivant et al., Oxazolone colitis: A murine model of T helper cell type 2 colitis treatable with antibodies to interleukin 4. J Exp Med. Nov. 16, 1998;188(10):1929-39.
Bruick et al., A conserved family of prolyl-4-hydroxylases that modify HIF. Science. Nov. 9, 2001;294(5545):1337-40. Epub Oct. 11, 2001.
Cunliffe et al., Assay of prolyl 4-hydroxylase by the chromatographic determination of [14C]succinic acid on ion-exchange minicolumns. Biochem J. Dec. 1, 1986;240(2):617-9.
Elkins et al., Structure of factor-inhibiting hypoxia-inducible factor (HIF) reveals mechanism of oxidative modification of HIF-1 alpha. J Biol Chem. Jan. 17, 2003;278(3):1802-6. Epub Nov. 21, 2002.
Epstein et al., C. elegans EGL-9 and mammalian homologs define a family of dioxygenases that regulate HIF by prolyl hydroxylation. Cell. Oct. 5, 2001;107(1):43-54.
Hewitson et al., Hypoxia-inducible factor (HIF) asparagine hydroxylase is identical to factor inhibiting HIF (FIH) and is related to the cupin structural family. J Biol Chem. Jul. 19, 2002;277(29):26351-5. Epub May 31, 2002.
Hirsilä et al., Characterization of the human prolyl 4-hydroxylases that modify the hypoxia-inducible factor. J Biol Chem. Aug. 15, 2003;278(33):30772-80. Epub Jun. 3, 2003.
Huang et al., Regulation of hypoxia-inducible factor 1alpha is mediated by an O2-dependent degradation domain via the ubiquitin-proteasome pathway. Proc Natl Acad Sci U S A. Jul. 7, 1998;95(14):7987-92.
Ivan et al., Biochemical purification and pharmacological inhibition of a mammalian prolyl hydroxylase acting on hypoxia-inducible factor. Proc Natl Acad Sci U S A. Oct. 15, 2002;99(21):13459-64. Epub Sep. 26, 2002.
Ivan et al., HIFalpha targeted for VHL-mediated destruction by proline hydroxylation: implications for O2 sensing. Science. Apr. 20, 2001;292(5516):464-8. Epub Apr. 5, 2001.
Jiang et al., Transactivation and inhibitory domains of hypoxia-inducible factor 1alpha. Modulation of transcriptional activity by oxygen tension. J Biol Chem. Aug. 1, 1997;272(31): 19253-60.
Karhausen et al., Epithelial hypoxia-inducible factor-1 is protective in murine experimental colitis. J Clin Invest. Oct. 2004;114(8):1098-106.
Kaule et al., Assay for 2-oxoglutarate decarboxylating enzymes based on the determination of [1-14C]succinate: application to prolyl 4-hydroxylase. Anal Biochem. Feb. 1, 1990;184(2):291-7.
Lando et al., Asparagine hydroxylation of the HIF transactivation domain a hypoxic switch. Science. Feb. 1, 2002;295(5556):858-61.
Lando et al., FIH-1 is an asparaginyl hydroxylase enzyme that regulates the transcriptional activity of hypoxia-inducible factor. Genes Dev. Jun. 15, 2002;16(12):1466-71.
Mahon et al., FIH-1: a novel protein that interacts with HIF-1alpha and VHL to mediate repression of HIF-1 transcriptional activity. Genes Dev. Oct. 15, 2001;15(20):2675-86.
Majamaa et al., Differences between collagen hydroxylases and 2-oxoglutarate dehydrogenase in their inhibition by structural analogues of 2-oxoglutarate. Biochem J. Jul. 1, 1985;229(1):127-33.
Majamaa et al., The 2-oxoglutarate binding site of prolyl 4-hydroxylase. Identification of distinct subsites and evidence for 2-oxoglutarate decarboxylation in a ligand reaction at the enzyme-bound ferrous ion. Eur J Biochem. Jan. 16, 1984;138(2):239-45.

(56) References Cited

OTHER PUBLICATIONS

Morris et al., Hapten-induced model of chronic inflammation and ulceration in the rat colon. Gastroenterology. Mar. 1989;96(3):795-803.

Myllyharju et al., Characterization of the iron- and 2-oxoglutarate-binding sites of human prolyl 4-hydroxylase. Embo J. Mar. 17, 1997;16(6):1173-80.

Neurath et al., TNBS-colitis. Int Rev Immunol. 2000;19(1):51-62.

Richard et al., Nonhypoxic pathway mediates the induction of hypoxia-inducible factor 1alpha in vascular smooth muscle cells. J Biol Chem. Sep. 1, 2000;275(35):26765-71.

Sandau et al., Induction of hypoxia-inducible-factor 1 by nitric oxide is mediated via the PI 3K pathway. Biochem Biophys Res Commun. Nov. 11, 2000;278(1):263-7.

Sodhi et al., MAPK and Akt act cooperatively but independently on hypoxia inducible factor-1alpha in rasV12 upregulation of VEGF. Biochem Biophys Res Commun. Sep. 14, 2001;287(1):292-300.

Srinivas et al., Characterization of an oxygen/redox-dependent degradation domain of hypoxia-inducible factor alpha (HIF-alpha) proteins. Biochem Biophys Res Commun. Jul. 5, 1999;260(2):557-61.

Tacchini et al., Hepatocyte growth factor signalling stimulates hypoxia inducible factor-1 (HIF-1) activity in HepG2 hepatoma cells. Carcinogenesis. Sep. 2001;22(9):1363-71.

Tanimoto et al., Mechanism of regulation of the hypoxia-inducible factor-1 alpha by the von Hippel-Lindau tumor suppressor protein. Embo J. Aug. 15, 2000;19(16):4298-309.

Taylor, Characterization and comparative analysis of the EGLN gene family. Gene. Sep. 5, 2001;275(1):125-32.

\* cited by examiner

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 1
ccaccacgct cttctgtcta c                                        21

<210> SEQ ID NO 2
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2
tgggctacag gcttgtcact                                          20

<210> SEQ ID NO 3
<211> LENGTH: 19
```

```
<212> TYPE: DNA
<213> ORGANISM: Artificial sequence
<220> FEATURE:
<223> OTHER INFORMATION: Synthetic oligonucleotide

<400> SEQUENCE: 3
ctaggcacca gggtgtgat                                               19

<210> SEQ ID NO 4
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 4
tgccagatct tctccatgtc                                              20
```

INFLAMMATORY BOWEL DISEASE THERAPIES

GOVERNMENT FUNDING

The invention was made with Government support under National Institutes of Health Grant No. DK50189. The Government has certain rights to this invention.

BACKGROUND OF THE INVENTION

Inflammatory bowel disease (IBD) is a collective term used to describe related inflammatory disorders of the gastrointestinal tract whose etiology is not completely understood. The two most common forms of IBD are ulcerative colitis (UC) and Crohn's disease (CD). For most patients, IBD is a chronic condition with symptoms lasting for months to years. The course of IBD varies widely, with intermittent periods of remission (i.e., inactive disease) followed by periods of acute illness (i.e., active disease). Onset of IBD is predominant in young adulthood but can occur at any age.

Ulcerative colitis affects the large intestine (colon) and rectum and involves the inner lining (e.g., the mucosal and sub-mucosal layer) of the intestinal wall. Crohn's disease may affect any section of the gastrointestinal tract (e.g., mouth, esophagus, stomach, small intestine, large intestine, rectum, anus, etc.) and may involve all layers of the intestinal wall. The clinical symptoms of IBD include rectal and/or intestinal bleeding, abdominal pain and cramping, diarrhea, and weight loss. In addition, IBD is a risk factor for colon cancer, and this risk for colon cancer increases significantly after eight to ten years of IBD.

IBD has no cure. Current therapies for IBD are directed at reducing the inflammatory process and at reducing the detrimental effects of the inflammatory process associated with the disease, and include administration of anti-inflammatory drugs (e.g., mesalamine, sulfasalazine, infliximab, adalimumab, prednisone, budesonide) and of immunosuppressive drugs (e.g., 6-mercaptopurine, azathioprine, cyclosporine). Such therapies are often associated with adverse side effects, such as nausea, vomiting, anorexia, dyspepsia, malaise, headaches, abdominal pain, fever, rash, pancreatitis, bone marrow suppression, formation of antibodies, infusion reactions, and increased opportunistic infections. In severe cases of IBD, or when drug therapy fails to relieve the symptoms of IBD, surgical procedures, including colectomy, proctocolectomy, and ileostomy, are used. Unfortunately, the available methods for treating IBD provide only treatment of symptoms rather than a substantial cure. These methods include either drug therapy accompanied by severe adverse side effects or invasive surgical treatments that further affect the patient's quality of life and, in addition, may further be life threatening.

SUMMARY

The present invention provides methods for treating inflammatory bowel disease in a subject in need. In various embodiments, the methods comprising treating inflammatory bowel disease in a subject having inflammatory bowel disease or at risk for having inflammatory bowel disease, the method comprising administering a therapeutically effective amount of an agent that inhibits hypoxia inducible factor (HIF) hydroxylase activity to the subject. In certain embodiments, the agent is a compound that inhibits HIF prolyl hydroxylase activity.

In some embodiments the inflammatory bowel disease is ulcerative colitis. In other embodiments the inflammatory bowel disease is Crohn's disease.

The agent that inhibits HIF hydroxylase may be, for instance, a HIF prolyl hydroxylase inhibitor. In some embodiments the HIF prolyl hydroxylase is EGLN1, EGLN2, or EGLN3. The agent that inhibits HIF hydroxylase in other embodiments is a HIF asparaginyl hydroxylase inhibitor, such as FIH. In yet other embodiments the agent that inhibits HIF hydroxylase is a compound that inhibits 2-oxoglutarate dioxygenase enzyme activity. In some preferred embodiments the agent that inhibits HIF hydroxylase is [(4-Hydroxy-7-phenylsulfanyl-isoquinoline-3-carbonyl)-amino]-acetic acid.

The agent that inhibits HIF hydroxylase in other embodiments is a HIF hydroxylase expression inhibitor. The HIF hydroxylase expression inhibitor may be, for instance, a small interfering nucleic acid such as a siRNA, a shRNA, an antisense oligonucleotide or a miRNA. In some embodiments the HIF hydroxylase expression inhibitor is a transgene that expresses a small interfering nucleic acid capable of inhibiting expression of a HIF hydroxylase gene.

In other aspects the invention is a kit having at least one container housing an agent that inhibits HIF hydroxylase and instructions for administering the agent to a subject having inflammatory bowel disease. The kit may include a second container housing an anti-IBD agent. In some embodiments the instructions indicate that the agent should be administered to a subject having ulcerative colitis or Crohn's disease.

A composition of an agent that inhibits HIF hydroxylase and an anti-IBD agent and a pharmaceutically acceptable carrier is provided according to other aspects of the invention.

The present invention provides methods for treating various forms of inflammatory bowel disease. In certain embodiments, the present invention provides methods for treating ulcerative colitis, the method comprising administering to a subject an effective amount of an agent that inhibits HIF hydroxylase activity. In other embodiments, methods are provided for treating Crohn's disease, the method comprising administering to a subject an effective amount of an agent that inhibits HIF hydroxylase activity. In certain embodiments, the agent is a compound that inhibits HIF prolyl hydroxylase activity. Methods for treating forms of inflammatory bowel disease, including, for example, diversion colitis, ischemic colitis, infectious colitis, chemical colitis, microscopic colitis (including collagenous colitis and lymphocytic colitis), atypical colitis, pseudomembranous colitis, fulminant colitis, autistic enterocolitis, indeterminate colitis, Behçet's disease, gastroduodenal CD, jejunoileitis, ileitis, ileocolitis, and Crohn's (granulomatous) colitis, are specifically provided by the present invention.

For purposes of the present invention, a subject in need is an individual who has or is at risk for having inflammatory bowel disease, or has one or more symptoms of inflammatory bowel disease. In certain embodiments, the subject having inflammatory bowel disease is a subject with any level or degree of disease activity, including a subject with mild disease activity, with moderate disease activity, or with severe disease activity. In other embodiments, the subject is a subject having one or more symptoms of inflammatory bowel disease, including, but not limited to, a subject having abdominal pain and cramping, diarrhea (including bloody diarrhea), rectal bleeding, fever, weight loss, fatigue, loss of appetite, loss of bodily fluids (dehydration) and nutrients, anemia due to intestinal bleeding, or ulcers (including ulcers occurring anywhere along the length of the intestines or rectum).

The present invention also provides methods for reducing or ameliorating a symptom of inflammatory bowel disease in a subject, the method comprising administering a therapeutically effective amount of an agent that inhibits HIF hydroxylase to the subject. In certain embodiments, the agent is a compound that inhibits HIF prolyl hydroxylase activity. In certain aspects, methods of the present invention are useful for reducing or ameliorating one or more of the following symptoms of inflammatory bowel disease: abdominal pain and cramping, diarrhea (including bloody diarrhea), rectal bleeding, fever, weight loss, fatigue, loss of appetite, loss of bodily fluids (dehydration) and nutrients, anemia due to intestinal bleeding, and ulcers (including ulcers occurring anywhere along the length of the intestines or rectum).

Methods for reducing intestinal permeability and for improving intestinal barrier function in a subject with inflammatory bowel disease are also provided by the present invention, the method comprising administering a therapeutically effective amount of an agent that inhibits HIF hydroxylase to the subject. In certain embodiments, the agent is a compound that inhibits HIF prolyl hydroxylase activity.

In some embodiments the agent that inhibits HIF hydroxylase selectively inhibits PHD-1, PHD-2, or PHD-3.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items. It must be noted that as used herein and in the appended claims, the singular forms "a," "an," and "the" include plural references unless context clearly dictates otherwise. Thus, for example, a reference to "a HIF-specific 2-oxoglutarate dioxygenase enzyme" may include a plurality of such enzymes; a reference to a "PHI" may be a reference to one or more PHIs, and so forth.

BRIEF DESCRIPTION OF THE DRAWINGS

The figures are illustrative only and are not required for enablement of the invention disclosed herein.

DETAILED DESCRIPTION

Figure 1:
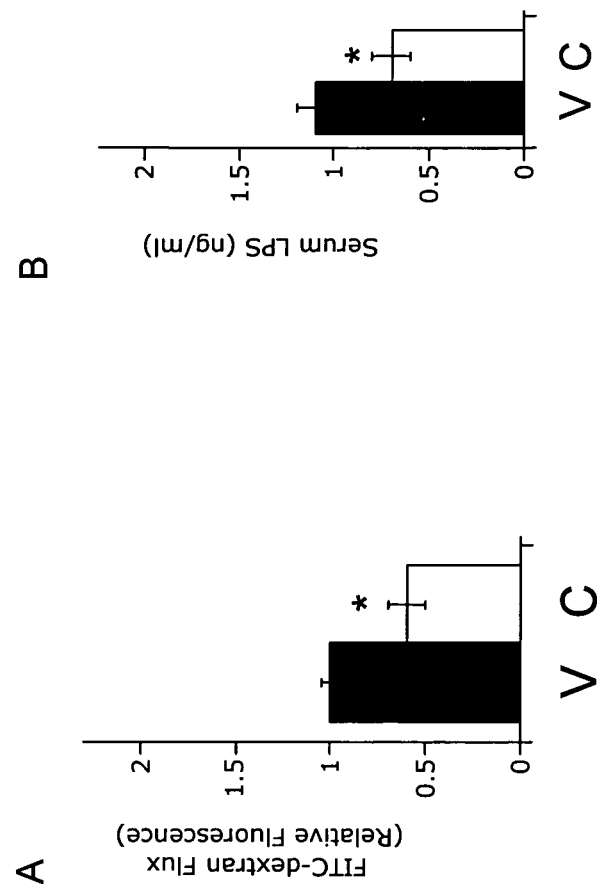
FIGS. 1A and 1B set forth data showing methods and compounds of the present invention reduced intestinal permeability and increased intestinal barrier function in an animal model of inflammatory bowel disease.

The present invention relates in some aspects to the discovery that HIF stabilization, by for instance, administration of an agent that inhibits HIF hydroxylase activity, is therapeutically effective in treating inflammatory bowel disease (IBD) in a subject. Thus, methods for treating IBD in a subject in need thereof are provided. Additionally, methods for ameliorating or reducing one or more symptoms of IBD in a subject or for the use of an agent that inhibits HIF hydroxylase activity in the manufacture of a medicament for the treatment of IBD are provided.

The term "inflammatory bowel disease" or "IBD" as used herein is a collective term describing inflammatory disorders of the gastrointestinal tract, the most common forms of which are ulcerative colitis and Crohn's disease. The present invention provides methods for treatment of IBD of any etiology. In certain embodiments, the present invention provides methods for treating ulcerative colitis, the method comprising administering to a subject an effective amount of an agent that inhibits HIF hydroxylase activity. In other embodiments, methods are provided for treating Crohn's disease, the method comprising administering to a subject an effective amount of an agent that inhibits HIF hydroxylase activity. In certain embodiments, the agent is a compound that inhibits HIF prolyl hydroxylase activity. Methods for treating other forms of IBD, including, for example, diversion colitis, ischemic colitis, infectious colitis, chemical colitis, microscopic colitis (including collagenous colitis and lymphocytic colitis), atypical colitis, pseudomembranous colitis, fulminant colitis, autistic enterocolitis, indeterminate colitis, Behçet's disease, gastroduodenal CD, jejunoileitis, ileitis, ileocolitis, Crohn's (granulomatous) colitis, irritable bowel syndrome, mucositis, radiation induced enteritis, short bowel syndrome, celiac disease, stomach ulcers, diverticulitis, pouchitis, proctitis, and chronic diarrhea are specifically contemplated by the present invention. Reference to IBD throughout the specification is often referred to in the specification as exemplary of gastrointestinal inflammatory conditions, and is not meant to be limiting.

As used herein, the term "symptoms of IBD" is herein defined as detected symptoms such as abdominal pain, diarrhea, rectal bleeding, weight loss, fever, loss of appetite, and other more serious complications, such as dehydration, anemia and malnutrition. A number of such symptoms are subject to quantitative analysis (e.g. weight loss, fever, anemia, etc.). Some symptoms are readily determined from a blood test (e.g. anemia) or a test that detects the presence of blood (e.g. rectal bleeding). The term "wherein said symptoms are reduced" refers to a qualitative or quantitative reduction in detectable symptoms, including but not limited to a detectable impact on the rate of recovery from disease (e.g. rate of weight gain). The diagnosis is typically determined by way of an endoscopic observation of the mucosa, and pathologic examination of endoscopic biopsy specimens.

The course of IBD varies, and is often associated with intermittent periods of disease remission (i.e., inactive disease) and disease exacerbation (i.e., active disease). Various methods have been described for characterizing disease activity and severity of IBD as well as response to treatment in subjects having IBD. (See, e.g., below.) Treatment according to the present invention is generally applicable to a subject having IBD of any level or degree of disease activity.

Table A below sets forth criteria useful for assessment of disease activity in subjects with ulcerative colitis according to Truelove. (See Truelove et al. (1955) Br Med J 2:1041-1048.) Using these criteria, disease activity can be characterized in a subject having IBD as mild disease activity or severe disease activity. Subjects who do not meet all the criteria for severe disease activity, and who exceed the criteria for mild disease activity (as presented below in Table A) are classified as having moderate disease activity.

TABLE A

|  | Mild Activity | Severe Activity |
|---|---|---|
| Daily Bowel Movements | ≤5 | >5 |
| Hematochezia | Small Amounts | Large Amounts |
| Temperature | <37.5° C. | ≥37.5° C. |
| Pulse | <90/min | ≥90/min |
| Erythrocyte Sedimentation Rate | <30 mm/h | ≥30 mm/h |
| Hemoglobin | >10 g/dl | ≤10 g/dl |

Other methods for assessing disease activity are known in the art, such as, for example, Crohn's Disease Activity Index (CDAI) (See Best et al. (1979) Gastroenterology 77:843-846.) A CDAI score of less than 150 is indicative of clinical disease remission (i.e., inactive disease); a score greater than 450 is indicative of severely active disease.

The present methods for treating IBD in a subject are useful for treating IBD at any level or degree of disease activity or severity. In certain embodiments, methods of the present invention are useful for treating IBD in a subject having mild disease activity. In other embodiments, methods of the present invention are useful for treating IBD in a subject having moderate disease activity. In yet other embodiments, methods are provided in the present invention for treating IBD in a subject having severe disease activity. Such methods provide benefit by reducing the level or degree of IBD disease activity in a subject, and include, for example, reducing the level or degree of disease activity in a subject having severe disease activity to a level or degree of moderate disease activity, mild disease activity, or no disease activity; reducing the level or degree of disease activity in a subject having moderate disease activity to a level or degree of mild disease activity or no disease activity; and, reducing the level or degree of disease activity in a subject having mild disease activity to a level or degree of no disease activity.

Methods for treating a subject having IBD, as described in the present invention, can also be applied at any point in the course of the disease. In certain embodiments, methods of the present invention are applied to a subject having IBD during a time period of remission (i.e., inactive disease). In such embodiments, the present methods provide benefit by extending the time period of remission (e.g., extending the period of inactive disease) or by preventing, reducing, or delaying the onset of active disease. In other embodiments, methods of the present invention are applied to a subject having IBD during a period of active disease. Such methods provide benefit by reducing the duration of the period of active disease, reducing or ameliorating one or more symptoms of IBD, or treating IBD.

Measures for determining efficacy of treatment of IBD in clinical practice have also been described and include, for example, the following: symptom control; fistula closure; extent of corticosteroid therapy required; and, improvement in quality of life. Heath-related quality of life (HRQL) can be assessed using the Inflammatory Bowel Disease Questionnaire (IBDQ), which is extensively used in clinical practice to assess quality of life in a subject with IBD. (See Guyatt et al. (1989) Gastroenterology 96:804-810.) Briefly, the IBDQ consists of 32 questions grouped into four categories as follows: bowel symptoms (10 items, including, for example, frequent or loose bowel movements, abdominal cramps, pain, etc.); systemic symptoms (5 items, including, for example, fatigue, lack of energy, poor sleep patterns, etc.); social functioning (5 items, including, for example, avoiding social events, canceling engagements, etc.); and emotional functioning (12 items, including, for example, anger, frustration, depression related to chronic disease, worry about surgery, etc.). For example, IBDQ scores for healthy subjects are generally about 210; IBDQ scores for subjects with active Crohn's disease are generally between about 125 and 130; IBDQ scores for subjects with Crohn's disease during quiescent (e.g., inactive disease) intervals are generally about 170. (See, e.g., Irvine et al. (1997) Am J Gastroenterol 92 (supp): 18S-24S.) Improvements in any of the foregoing response criteria are specifically provided by the methods of the present invention.

Symptoms of IBD include abdominal pain and cramping, diarrhea (including bloody diarrhea), rectal bleeding, intestinal bleeding, fever, weight loss, fatigue, loss of appetite, loss of bodily fluids (dehydration) and nutrients, anemia due to intestinal bleeding, and ulcers (along the length of the intestines or rectum). Methods for reducing or ameliorating one or more symptoms of IBD are provided by the present invention, the methods comprising administering to a subject having IBD an agent that inhibits HIF hydroxylase activity. In certain embodiments, the agent is a compound that inhibits HIF prolyl hydroxylase activity. In certain aspects, methods of the present invention are useful for reducing or ameliorating one or more of the following symptoms of IBD: abdominal pain and cramping, diarrhea (including bloody diarrhea), rectal bleeding, fever, weight loss, fatigue, loss of appetite, loss of bodily fluids (dehydration) and nutrients, anemia due to intestinal bleeding, and ulcers (including ulcers occurring anywhere along the length of the intestines or rectum).

Under normal (e.g., healthy, non-disease) conditions, epithelial cells lining the intestine provide a critical barrier (i.e., intestinal barrier function) between the intestinal lumen and the sub-epithelial mucosa, providing intestinal barrier protection. In IBD, the integrity and normal functioning of the intestinal epithelial cells is impaired. Impaired functioning of the intestinal epithelial cells is associated with adverse pathological outcomes, including loss of tight junction integrity, loss of selective barrier function, and increased intestinal permeability. Methods of the present invention reduced intestinal permeability in an animal model of inflammatory bowel disease. (See Example 2.) Therefore, in certain embodiments, the present invention provides methods useful for reducing intestinal permeability in a subject having IBD, the methods comprising administering to the subject an effective amount of an agent that inhibits HIF hydroxylase activity. In other embodiments, the present invention provides methods for improving or maintaining intestinal barrier function in a subject having IBD, the methods comprising administering to the subject an effective amount of an agent that inhibits HIF hydroxylase activity. In certain aspects, the agent is a compound that inhibits HIF prolyl hydroxylase activity.

Improvements in other symptoms and pathological parameters associated with IBD are also specifically provided by the methods of the present invention. Methods of the present invention reduced weight loss (See Example 3), reduced colon shortening (See Example 4), reduced villous blunting of the intestine (See Example 5), reduced thickening of the intestinal wall (See Example 5), and maintained or restored intestinal tissue architecture (See Example 5) in an animal model of inflammatory bowel disease.

The compounds of the invention in some aspects inhibit HIF hydroxylase activity. The inhibition can be direct or indirect, can be competitive or non-competitive, etc. Hypoxia inducible factor (HIF) is a transcriptional complex that plays a key role in mammalian oxygen homeostasis and regulates angiogenic genes such as VEGF. HIF is a heterodimer containing an oxygen-regulated α subunit (HIFα) and a constitutively expressed β subunit (HIFβ), also known as aryl hydrocarbon receptor nuclear transporter (ARNT). In the presence of oxygen, posttranslational modification by prolyl hydroxylation in the oxygen-dependent degradation domain (ODD) targets HIF-1 α subunits for proteasomal degradation via binding to the VHL (von Hippel-Lindau tumor suppressor protein), Elongin C/B, Cul2, Rbx1 ubiquitin E3 ligase complex. However, during ischemia, the hydroxylation of HIF-1 α is inhibited and HIF-1 α binds to ARNT to form a functional transcriptional activator that turns on genes with hypoxic response elements (e.g. VEGF, EPO, glycolytic enzymes). Proline hydroxylation of HIF-1α is a required step for ubiquitinylation by the E3 ligase complex and is accomplished by at least three enzymes, EGLN1, EGLN2, and/or EGLN3.

The term "HIFα" refers to the α subunit of hypoxia inducible factor protein. HIFα may be any human or other mammalian protein, or fragment thereof, including human HIF-1α (Genbank Accession No. Q16665), HIF-2α (Genbank Accession No. AAB41495), and HIF-3α (Genbank Accession No. AAD22668); murine HIF-1α (Genbank Accession No. Q61221), HIF-2α (Genbank Accession No. BAA20130 and AAB41496), and HIF-3α (Genbank Accession No. AAC72734); rat HIF-1α (Genbank Accession No. CAA70701), HIF-2α (Genbank Accession No. CAB96612), and HIF-3α (Genbank Accession No. CAB96611); and bovine HIFα (Genbank Accession No. BAA78675). HIFα may also be any non-mammalian protein or fragment thereof, including *Xenopus laevis* HIF-1α (Genbank Accession No. CAB96628), *Drosophila melanogaster* HIF-1α (Genbank Accession No. JC4851), and chicken HIF-1α (Genbank Accession No. BAA34234). HIFα gene sequences may also be obtained by routine cloning techniques, for example by using all or part of a HIFα gene sequence described above as a probe to recover and determine the sequence of a HIFα gene in another species.

A fragment of HIFα includes any fragment retaining at least one functional characteristic of HIFα. Fragments of HIFα include, e.g., the regions defined by human HIF-1α from amino acids 401 to 603 (Huang et al., supra), amino acid 531 to 575 (Jiang et al. (1997) J Biol. Chem 272:19253-19260), amino acid 556 to 575 (Tanimoto et al., supra), amino acid 557 to 571 (Srinivas et al. (1999) Biochem Biophys Res. Commun 260:557-561), and amino acid 556 to 575 (Ivan and Kaelin (2001) Science 292:464-468). Further, HIFα fragments include any fragment containing at least one occurrence of the motif LXXLAP, e.g., as occurs in the human HIF-1α native sequence at $L_{397}$TLLAP and $L_{559}$EMLAP.

Several investigators have studied the mechanism of interaction between HIFα and pVHL. An oxygen-dependent degradation domain (ODD) within HIF-1α from residue 401 to 603 was originally identified as sufficient to confer oxygen-dependent instability to chimeric protein constructs. A domain containing a portion of the ODD, from residue 526 to 652, was found to be required for pVHL-dependent degradation. Further, mutation of $P_{564/7}$ to aspartic acids or mutation of $K_{532}$ to arginine within a region conserved among HIFα homologs (residue 556 to 574 in HIF-1α) rendered the full-length HIFα protein stable under normoxic conditions and resistant to pVHL-mediated degradation. (Huang, et al., (1998) Proc. Natl. Acad. Sci. USA, 95:7987-7992; and Tanimoto, et al., (2000) EMBO. J. 19:4298-4309.)

HIFα levels are increased by a number of factors that mimic hypoxia, including iron chelators such as desferrioxamine (DFO) and divalent metal salts such as $CoCl_2$ HIFα levels are increased by angiotensin II, thrombin, and platelet-derived growth factor under normoxic conditions using a mechanism involving reactive oxygen species. Reports have also suggested HIFα is regulated by phosphorylation through pathways involving nitric oxide-activated phosphatidylinositol 3'-kinase (PI3K), hepatocyte growth factor, or mitogen-activated protein kinase. Glycogen-synthase kinase, which is a downstream target of PI3K, directly phosphorylates the HIFα ODD domain. (Richard, et al., (2000) J. Biol. Chem., 275:26765-26771; Sandau, et al., (2000) Biochem. Biophys. Res. Commun. 278:263-267; Tacchini, et al., (2001) Carcinogenesis, 22:1363-1371; and Sodhi, et al., (2001) Biochem. Biophys. Res. Commun., 287:292-300.)

The therapeutic methods of the invention involve the production of stabilized HIF in cells. Thus the methods of the invention can be carried out using HIF agonists or HIF hydroxylase antagonists. The term "agonist" refers to a molecule that increases or prolongs the duration of the effect of a particular molecule. Agonists may include proteins, nucleic acids, carbohydrates, or any other molecules that increase the effect(s) of the target molecule. The term "antagonist" refers to a molecule that decreases the extent or duration of the effect of the biological or immunological activity of a particular molecule. Antagonists may include proteins, nucleic acids, carbohydrates, antibodies, or any other molecules that decrease the effect(s) of the target molecule.

HIF hydroxylase antagonists are agents that inhibit HIF hydroxylase. As used herein an agent that inhibits HIF hydroxylase is a compound that affects the expression or activity of HIF hydroxylase and reduces the ability of the hydroxylase to interfere with the stability of HIF. Thus, agents that inhibit HIF hydroxylase activity result in the increased stability and activity of HIF. The term "HIF hydroxylase" refers to any enzyme that is capable of hydroxylating an amino acid residue in the HIF protein, particularly the HIFα subunit. Preferably, the amino acid residue is a proline and/or an asparagine residue.

The term "HIF asparaginyl hydroxylase" refers to any enzyme that is capable of hydroxylating an asparagine residue in the HIF protein. Preferably, the asparagine residue hydroxylated by HIF asparaginyl hydroxylase includes, e.g., the $N_{803}$ residue of HIF-1α or a homologous asparagine residue in another HIFα isoform. HIF asparaginyl hydroxylase includes Factor Inhibiting HIF (FIH), an asparaginyl hydroxylase responsible for regulating transactivation of HIFα (GenBank Accession No. AAL27308; Mahon et al. (2001) Genes Dev 15:2675-2686; Lando et al. (2002) Science 295:858-861; and Lando et al. (2002) Genes Dev 16:1466-1471. Also, see, Elkins et al. (2002) J Biol Chem C200644200.). In other embodiments, the HIF hydroxylase is a HIF asparaginyl hydroxylase, such as, for example, FIH.

The terms "HIF prolyl hydroxylase" and "HIF PH" refer to any enzyme that is capable of hydroxylating a proline residue in the HIF protein. Preferably, the proline residue hydroxylated by HIF PH includes the proline found within the motif LXXLAP, e.g., as occurs in the human HIF-1α native sequence at $L_{397TL}$LAP and $L_{559}$EMLAP. HIF PH includes members of the Egl-Nine (EGLN) gene family described by Taylor (2001, Gene 275:125-132), and characterized by Aravind and Koonin (2001, Genome Biol 2:RESEARCH0007), Epstein et al. (2001, Cell 107:43-54), and Bruick and McKnight (2001, Science 294:1337-1340). Examples of HIF PH enzymes include human SM-20 (EGLN1) (GenBank Accession No. AAG33965; Dupuy et al. (2000) Genomics 69:348-54), EGLN2 isoform 1 (GenBank Accession No. CAC42510; Taylor, supra), EGLN2 isoform 2 (GenBank Accession No. NP_060025), and EGLN3 (GenBank Accession No. CAC42511; Taylor, supra); mouse EGLN1 (GenBank Accession No. CAC42515), EGLN2 (GenBank Accession No. CAC42511), and EGLN3 (SM-20) (GenBank Accession No. CAC42517); and rat SM-20 (GenBank Accession No. AAA19321). Additionally, HIF PH may include *Caenorhabditis elegans* EGL-9 (GenBank Accession No. AAD56365) and *Drosophila melanogaster* CG1114 gene product (GenBank Accession No. AAF52050). HIF PH also includes any active fragment of the foregoing full-length proteins. In various embodiments, the HIF hydroxylase is a HIF prolyl hydroxylase, such as, for example, EGLN1, EGLN2, or EGLN3, etc.

EGLN are 2-oxoglutarate dioxygenase enzymes that, among other potential substrates, are known to hydroxylate specific proline residues in HIFα proteins. The proline residues hydroxylated by EGLN include the proline residues that occur in the human HIF-1α native sequence at residues 402 ($P_{402}$) and 564 ($P_{564}$), and corresponding proline residues in HIFα subunits obtained from another species as shown, e.g., in FIG. 1. In preferred embodiments, the EGLN utilized in the assay is selected from members of the Egl-9 enzyme family described by Taylor (supra), and characterized by Aravind and Koonin (supra), Epstein et al. (supra), and Bruick and McKnight (supra). In some embodiments of the present invention, the EGLN enzyme may be selected from an isoform of EGLN1, EGLN2, and/or EGLN3. The EGLN1 isoform may be selected from the group that includes, but is not limited to, human EGLN1 (hEGLN1, GenBank Accession No. AAG33965; Dupuy et al. (2000) Genomics 69:348-54), mouse EGLN1 (GenBank Accession No. CAC42515), and rat EGLN1 (GenBank Accession No. P59722); the EGLN2 isoform may be selected from the group that includes, but is not limited to, human EGLN2 isoform 1 (GenBank Accession No. CAC42510; Taylor, supra), human EGLN2 isoform 3 (GenBank Accession No. NP_542770), mouse EGLN2 (GenBank Accession No. CAC42516), and rat EGLN2 (GenBank Accession No. AA046039); and the EGLN3 isoform may be selected from the group that includes, but is not limited to, human EGLN3 (GenBank Accession No. CAC42511; Taylor, supra), mouse EGLN3 (GenBank Accession No. CAC42517); and rat EGLN3 (SM-20) (GenBank Accession No. AAA19321). In other embodiments of the present invention, EGLN may include *Caenorhabditis elegans* EGL-9 (GenBank Accession No. AAD56365) and *Drosophila melanogaster* CG1114 gene product (GenBank Accession No. AAF52050).

Thienopyridines substituted at the 2-position by alkyl, aryl, halogen, hydrogen or arylthioxy groups, the 4-position by alkyl, aryl, cyano, halogen and heteroaryl groups, in the 6-position by a secondary amide group and the 7-position by hydroxyl have been described as HIF modulators in WO2006094292, which is incorporated by reference.

The 2-oxoglutarate dioxygenase enzymes are responsible for various physiological processes associated with normal cellular maintenance and cellular response to a changing environment and stress. The 2-oxoglutarate dioxygenases are non-heme-Fe(II)-dependent oxygenases that modify, e.g., by hydroxylation, various substrates. In addition to iron, the 2-oxoglutarate dioxygenases require oxygen, 2-oxoglutarate, and ascorbic acid for their activity. Some of the best-studied family members include the collagen modifying enzymes lysine hydroxylase (EC 1.14.11.4), prolyl 3-hydroxylase (EC 1.14.11.7), and the α-subunit of prolyl 4-hydroxylase (P4H; EC 1.14.11.2). (See, e.g., Majamaa et al. (1985) Biochem J 229:127-133; Myllyharju and Kivirikko (1997) EMBO J 16:1173-1180.).

All of the 2-oxoglutarate dioxygenase enzymes utilize a common catalytic mechanism that involves coordination of 2-oxoglutarate and dioxygen to enzyme-bound iron. The oxygen is subsequently cleaved, and one atom of oxygen is transferred to 2-oxoglutarate to produce carbon dioxide and succinate. The remaining Fe-bound atom of oxygen then modifies a second substrate; in the case of P4H, a proline residue residing within a particular amino acid sequence framework of collagen is oxidized to hydroxyproline. Thus, the enzymes of this family require iron, use 2-oxoglutarate and dioxygen as substrates, and produce succinate and carbon dioxide as products. The additional substrate utilized by each enzyme differs between family members, and thereby distinguishes the various members of the family and provides a unique context for each reaction catalyzed. The enzymes also require ascorbic acid as a cofactor to prevent enzyme inactivation.

In some aspects, compounds of the present invention include, for example, structural mimetics of 2-oxoglutarate. Such compounds may inhibit a HIF hydroxylase competitively with respect to 2-oxoglutarate and noncompetitively with respect to iron. (Majamaa et al. (1984) Eur J Biochem 138:239-245; and Majamaa et al. Biochem J 229:127-133.) Structural mimetics of 2-oxoglutarate are described for instance in US published patent application 2006/0276477, which is incorporated by reference for such teachings.

Such compounds include for instance, pyridine-2-carboxamides, quinoline-2-carboxamides, and isoquinoline-3-carboxamides. In some embodiments these compounds are selected from the group consisting of: [4-Hydroxy-1-(naphthalen-2-yloxy)-isoquinoline-3-carbonyl]-amino}-acetic acid; {[4-Hydroxy-1-(pyridin-3-yloxy)-isoquinoline-3-carbonyl]-amino}-acetic acid; {[4-Hydroxy-1-(4-methoxy-phenoxy)-isoquinoline-3-carbonyl]-amino-}-acetic acid; {[4-Hydroxy-1-(3-methoxy-phenoxy)-isoquinoline-3-carbonyl]-amino}-acetic acid; {[1-(3-Fluoro-phenoxy)-4-hydroxy-isoquinoline-3-carbonyl]-amino}-acetic acid; {[1-(4-Fluoro-phenoxy)-4-hydroxy-isoquinoline-3-carbonyl]-amino-}-acetic acid; {[1-(2-Fluoro-phenoxy)4-hydroxy-isoquinoline-3-carbonyl]-amino}-acetic acid; {[4-Hydroxy-1-(2-methoxy-phenoxy)-isoquinoline-3-carbonyl]-amino}-acetic acid; {[1-(4-Acetylamino-phenoxy)-4-hydroxy-isoquinoline-3-carbonyl]-amino}-acetic acid; {[4-Hydroxy-1-(4-methanesulfonylamino-phenoxy)-isoquinoline-3-carbonyl]amino}-acetic acid; [(4-Hydroxy-1-phenylamino-isoquinoline-3-carbonyl)-amino]-acetic acid; {[4-Hydroxy-6-(pyridin-3-yloxy)-isoquinoline-3-carbonyl]-amino}-acetic acid; {[4-Hydroxy-7-(pyridin-3-yloxy)-isoquinoline-3-carbonyl]-amino}-acetic acid; [(1-Chloro-4-methoxy-isoquinoline-3-carbonyl)-amino]-acetic acid; [(1-Chloro-4-ethoxy-isoquinoline-3-carbonyl)-amino]-acetic acid; [(4-Hydroxy-1-methoxy-isoquinoline-3-carbonyl)-amino]acetic acid; [(1-Ethoxy4-hydroxy-isoquinoline-3-carbonyl)-amino]-acetic acid; [(4-Acetoxy-1-phenyl-isoquinoline-3-carbonyl)-amino]-acetic acid; [(4-Hydroxy-1-phenyl-isoquinoline-3-carbonyl)-amino]-acetic acid; [(1-Ethoxy4-phenyl-isoquinoline-3-carbonyl)-amino]-acetic acid; (1-Chloro-4-phenyl-isoquinoline-3-carbonyl)-amino]-acetic acid; [(4-Phenyl-isoquinoline-3-carbonyl)-amino]-acetic acid; [(4-Hydroxy-1-methyl-isoquinoline-3-carbonyl)-amino]-acetic acid; [(4-Hydroxy-1-methoxymethyl-isoquinoline-3-carbonyl)-amino]-acetic acid; [(1-Dimethylcarbamoyl-4-hydroxy-isoquinoline-3-carbonyl)-amino]-acetic acid; [(4-Hydroxy-1-methyl-6-phenoxy-isoquinoline-3-carbonyl)-amino]-acetic acid; [(4-Hydroxy-1-methyl-7-phenoxy-isoquinoline-3-carbonyl)-amino]-acetic acid; [(4-Benzyloxy-1-methyl-7-phenoxy-isoquinoline-3-carbonyl)-amino-]-acetic acid; [(4-Ethoxy-1-methyl-7-phenoxy-isoquinoline-3-carbonyl)-amino]-acetic acid; [(1-Dimethylcarbamoyl-4-hydroxy-7-phenoxy-isoquinoline-3-carbonyl)-amino]-acetic acid; [(4-Hydroxy-1-methoxymethyl-7-phenoxy-isoquinoline-3-carbonyl)-amino]-acetic acid; [(4-Hydroxy-1-p-tolyl-isoquinoline-3-carbonyl)-amino]-acetic acid; {[7-(4-Fluoro-phenoxy)-4-hydroxy-1-methyl-isoquinoline-3-carbonyl]-amino}-acetic acid; {[1-Chloro-4-hydroxy-7-(4-methoxy-phenoxy)-isoquinoline-3-carbonyl]-amino-}-acetic acid; {[4-Hydroxy-7-(4-methoxy-phenoxy)-isoquinoline-3-carbonyl]amino}-acetic acid; {[1-Chloro-4-hydroxy-6-(4-methoxy-phenoxy)-isoquinoline-3-carbonyl]-amino}-acetic acid; {[4-Hydroxy-6-(4-methoxy-phenoxy)-isoquinoline-3-carbonyl]-amino}-acetic acid; {[1-Chloro-4-hydroxy-7-(4-trifluoromethyl-phenoxy)-isoquinoline-3-carbonyl]-amino}-acetic acid; {[4-Hydroxy-7-(4-trifluoromethyl-phenoxy)-isoquinoline-3-carbonyl]-amino)-acetic acid; {[1-Chloro-4-hydroxy-6-(4-trifluoromethyl-phenoxy)-isoquinoline-3-carbonyl]-amino}-acetic acid; {[4-Hydroxy-6-(4-trifluoromethyl-phenoxy)-isoquinoline-3-carbonyl]-amino}-acetic acid; {[1-Chloro-7-(4-fluoro-phenoxy)-4-hydroxy-isoquinoline-3-carbonyl]-amino}-acetic acid; {[7-(4-Fluoro-phenoxy)-4-hydroxy-isoquinoline-3-carbonyl]-amino}-acetic acid; {[1-Chloro-6-(4-fluoro-phenoxy)-4-hydroxy-isoquinoline-3-carbonyl]-amino}-acetic acid; {[6-(4-Fluoro-phenoxy)-4-hydroxy-isoquinoline-3-carbonyl]-amino}-acetic acid; {[4-Hydroxy-7-(pyridin4-ylsulfanyl)-isoquinoline-3-carbonyl]-amino}-acetic acid; {[4-Hydroxy-6-(pyridin4-ylsulfanyl)-isoquinoline-3-carbonyl]-amino}-acetic acid; [(7-Benzenesulfinyl4-hydroxy-isoquinoline-3-carbonyl)-amino]-acetic acid; [(7-Benzenesulfonyl-4-hydroxy-isoquinoline-3-carbonyl)-amino]-acetic acid; [(6-Benzenesulfinyl-4-hydroxy-isoquinoline-3-carbonyl)-amino]-acetic acid; [(6-Benzenesulfonyl-4-hydroxy-isoquinoline-3-carbonyl)-amino]-acetic acid; [(6-Amino4-hydroxy-isoquinoline-3-carbonyl)-amino]-acetic acid; {[4-Hydroxy-7-(4-methoxy-benzenesulfonylamino)-isoquinoline-3-carbonyl]-amino}-acetic acid; {[4-Hydroxy-7-(3-phenyl-ureido)-isoquinoline-3-carbonyl]-amino}-acetic acid; {[4-Hydroxy-6-(3-phenyl-ureido)-isoquinoline-3-carbonyl]-amino}-acetic acid; [(4-Hydroxy-1-phenylsulfanyl-isoquinoline-3-carbonyl)-amino]-acetic acid; {[1-(4-Chloro-phenylsulfanyl)4-hydroxy-isoquinoline-3-carbonyl]-amino}-acetic acid; [(4-Hydroxy-1-p-tolylsulfanyl-isoquinoline-3-carbonyl)-amino]-acetic acid; {[4-Hydroxy-1-(pyridin-2-ylsulfanyl)-isoquinoline-3-carbonyl]-amino-}-acetic acid; {[4-Hydroxy-1-(3-methoxy-phenylsulfanyl)-isoquinoline-3-carbonyl]-amino}-acetic acid; {[4-Hydroxy-1-(2-methoxy-phenylsulfanyl)-isoquinoline-3-carbonyl]-amino}-acetic acid; {[4-Hydroxy-1-(naphthalen-2-ylsulfanyl)-isoquinoline-3-carbonyl]-amino}-acetic acid; [(1-Benzenesulfinyl-4-hydroxy-isoquinoline-3-carbonyl)-amino]-acetic acid; [(1-Benzenesulfonyl4-hydroxy-isoquinoline-3-carbonyl)-amino]-acetic acid; {[4-Hydroxy-7-(pyridin-2-ylsulfanyl)-isoquinoline-3-carbonyl]-amino-}-acetic acid; {[4-Hydroxy-6-(pyridin-2-ylsulfanyl)-isoquinoline-3-carbonyl]-amino}-acetic acid; [(1-Chloro-4-hydroxy-6,7-diphenoxy-isoquinoline-3-carbonyl)-amino-]-acetic acid; [(4-Hydroxy-6,7-diphenoxy-isoquinoline-3-carbonyl)-amino]-acetic acid; ({4-Hydroxy-7-[4-(toluene-4-sulfonylamino)-phenoxy]-isoquinoline-3-carbonyl}-amino)-acetic acid; {[4-Hydroxy-7-(4-nitro-phenoxy)-isoquinoline-3-carbonyl]-amino}-acetic acid; [(4-Mercapto-7-phenoxy-isoquinoline-3-carbonyl)-amino]-acetic acid; [(4-Mercapto-7-trifluoromethyl-isoquinoline-3-carbonyl)-amino]-acetic acid; {[7-(4-Benzenesulfonylamino-phenoxy)-4-hydroxy-isoquinoline-3-carbonyl]-amino-acetic acid; {[4-Hydroxy-7-(4-methanesulfonylamino-phenoxy)-isoquinoline-3-carbonyl]-amino}-acetic acid; [7-(4-Chloro-phenoxy)4-hydroxy-isoquinoline-3-carbonyl]-amino}-acetic acid; {[6-(4-Chloro-phenoxy)-4-hydroxy-isoquinoline-3-carbonyl]-amino}-acetic acid; {[6-(3-Fluoro-5-methoxy-phenoxy)-4-hydroxy-isoquinoline-3-carbonyl]-amino}-acetic acid; {[7-(3-Fluoro-5-methoxy-phenoxy)-4-hydroxy-isoquinoline-3-carbonyl]-amino-}-acetic acid; {[7-(3,4-Difluoro-phenoxy)-4-hydroxy-isoquinoline-3-carbonyl]-amino}-acetic acid; {[6-(3,4-Difluoro-phenoxy)-4-hydroxy-isoquinoline-3-carbonyl]-amino}-acetic acid; {[4-Hydroxy-7-(4-trifluoromethoxy-phenoxy)-isoquinoline-3-carbonyl]-amino-acetic acid; {[4-Hydroxy-6-(4-trifluoromethoxy-phenoxy)-isoquinoline-3-carbonyl]-amino-acetic acid; 2-(S)-{[7-(4-Chloro-phenoxy)4-hydroxy-isoquinoline-3-carbonyl]-amino}-propionic acid; 2-(S)-{[6-(4-Chloro-phenoxy)-4-hydroxy-isoquinoline-3-carbonyl]-amino}-propionic acid; 2-{[7-(3,4-Difluoro-phenoxy-4-hydroxy-isoquinoline-3-carbonyl]-amino}-propionic acid; 2-(S)-[(4-Hydroxy-7-phenylsulfanyl-isoquinoline-3-carbonyl)-amino]-propionic acid; 2-(R)-[(4-Hydroxy-7-phenylsulfanyl-isoquinoline-3-carbonyl)-amino]-propionic acid; 2-(R)-[(4-Hydroxy-7-phenoxy-isoquinoline-3-carbonyl)-amino]-propionic acid; 2-(S)-{[4-Hydroxy-7-(4-methoxy-phenoxy)-isoquinoline-3-carbonyl]-amino}-propionic acid; 2-(S)-[(7-Benzenesulfonyl-4-hydroxy-isoquinoline-3-carbonyl)-amino]-propionic acid; (R)-2-[(4-Hydroxy-1-methoxymethyl-7-phenoxy-isoquinoline-3-carbonyl)-amino]-propionic acid; (S)-2-[(4-Hydroxy-1-methoxymethyl-7-phenoxy-isoquinoline-3-carbonyl)-amino]-propionic acid; (S)-2-[(4-Mercapto-7-phenoxy-isoquinoline-3-carbonyl)-amino]-propionic acid; (S)-2-{[1-

(4-Chloro-phenylsulfanyl)4-hydroxy-isoquinoline-3-carbonyl]-amino}-propionic acid; (R)-2-{[1-(4-Chloro-phenylsulfanyl)4-hydroxy-isoquinoline-3-carbonyl]-amino}-propionic acid; [(4-Hydroxy-7-phenylsulfanyl-isoquinoline-3-carbonyl)-amino]-acetic acid; [(4-Hydroxy-6-phenylsulfanyl-isoquinoline-3-carbonyl)-amino]-acetic acid; [(1-Chloro-4-hydroxy-7-phenylsulfanyl-isoquinoline-3-carbonyl)-amino]-acetic acid; [(1-Chloro-4-hydroxy-6-phenylsulfanyl-isoquinoline-3-carbonyl)-amino]-acetic acid; [(1-bromo-4-hydroxy-7-phenylsulfanyl-isoquinoline-3-carbonyl)-amino]-acetic acid; [(1-Bromo-4-hydroxy-6-phenylsulfanyl-isoquinoline-3-carbonyl)-amino]-acetic acid; [(4-Hydroxy-7-phenoxy-isoquinoline-3-carbonyl)-amino]-acetic acid; [(4-Hydroxy-6-phenoxy-isoquinoline-3-carbonyl)-amino]-acetic acid; [(1-Chloro-4-hydroxy-7-phenoxy-isoquinoline-3-carbonyl)-amino]-acetic acid; [(1-Chloro-4-hydroxy-6-phenoxy-isoquinoline-3-carbonyl)-amino]-acetic acid; [(1-Bromo-4-hydroxy-7-phenoxy-isoquinoline-3-carbonyl)-amino]-acetic acid; [(1-Bromo-4-hydroxy-6-phenoxy-isoquinoline-3-carbonyl)-amino]-acetic acid; {[7-(2,6-Dimethyl-phenoxy)-4-hydroxy-isoquinoline-3-carbonyl]-amino}-acetic acid; {[1-Chloro-7-(2,6-dimethyl-phenoxy)-4-hydroxy-isoquinoline-3-carbonyl]-amino}-acetic acid; {[1-bromo-7-(2,6-dimethyl-phenoxy)-4-hydroxy-isoquinoline-3-carbonyl]-amino}-acetic acid; [(1-bromo-7-chloro-4-hydroxy-isoquinoline-3-carbonyl)-amino]-acetic acid; [(1-bromo-6-chloro-4-hydroxy-isoquinoline-3-carbonyl)-amino]-acetic acid; [(1-bromo-4-hydroxy-7-trifluoromethyl-isoquinoline-3-carbonyl)-amino]-acetic acid; [(1-bromo-4-hydroxy-6-trifluoromethyl-isoquinoline-3-carbonyl)-amino]-acetic acid; [(4-Hydroxy-1-phenoxy-isoquinoline-3-carbonyl)-amino]-acetic acid; [(1,7-dibromo-4-hydroxy-isoquinoline-3-carbonyl)-amino]-acetic acid; [(7-bromo-1-chloro-4-hydroxy-isoquinoline-3-carbonyl)-amino]-acetic acid; [(6-bromo-4-hydroxy-isoquinoline-3-carbonyl)-amino]-acetic acid; [(1-bromo-7-fluoro-4-hydroxy-isoquinoline-3-carbonyl)-amino]-acetic acid; [(7-Fluoro-4-hydroxy-isoquinoline-3-carbonyl)-amino]-acetic acid; [(1-Chloro-7-fluoro-4-hydroxy-isoquinoline-3-carbonyl)-amino]-acetic acid; [(1-Chloro-4-hydroxy-benzo[g]isoquinoline-3-carbonyl)-amino]-acetic acid; [(1-bromo-4-hydroxy-isoquinoline-3-carbonyl)-amino]-acetic acid; [(4-Hydroxy-6-phenyl-isoquinoline-3-carbonyl)-amino]-acetic acid; [(4-Hydroxy-7-phenyl-isoquinoline-3-carbonyl)-amino]-acetic acid; [(1-Chloro-4-hydroxy-6-phenyl-isoquinoline-3-carbonyl)-amino]-acetic acid; [(1-Chloro-4-hydroxy-7-phenyl-isoquinoline-3-carbonyl)-amino]-acetic acid; [(1-Bromo-4-hydroxy-6-phenyl-isoquinoline-3-carbonyl)-amino]-acetic acid; [(1-bromo-4-hydroxy-7-phenyl-isoquinoline-3-carbonyl)-amino]-acetic acid; [(4-Hydroxy-5-phenyl-isoquinoline-3-carbonyl)-amino]-acetic acid; [(4-Hydroxy-8-phenyl-isoquinoline-3-carbonyl)-amino]-acetic acid; [(1-Chloro-4-hydroxy-5-phenyl-isoquinoline-3-carbonyl)-amino]-acetic acid; [(1-Chloro-4-hydroxy-8-phenyl-isoquinoline-3-carbonyl)-amino]-acetic acid; [(1-bromo-4-hydroxy-5-phenyl-isoquinoline-3-carbonyl)-amino]-acetic acid; [(1-bromo-4-hydroxy-8-phenyl-isoquinoline-3-carbonyl)-amino]-acetic acid; [(1-Ethylsulfanyl-4-hydroxy-isoquinoline-3-carbonyl)-amino]-acetic acid; {[4-Hydroxy-1-(4-methoxy-phenylsulfanyl)-isoquinoline-3-carbonyl]-amino}-acetic acid; [(1-Chloro-4-hydroxy-7-iodo-isoquinoline-3-carbonyl)-amino]-acetic acid; [(1-Chloro-4-hydroxy-6-iodo-isoquinoline-3-carbonyl)-amino]-acetic acid; [(4-Hydroxy-7-iodo-isoquinoline-3-carbonyl)-amino]-acetic acid; [(1-bromo-4-hydroxy-7-methyl-isoquinoline-3-carbonyl)-amino]-acetic acid; [(1-bromo-7-butoxy-4-hydroxy-isoquinoline-3-carbonyl)-amino]-acetic acid; [(1-bromo-6-butoxy-4-hydroxy-isoquinoline-3-carbonyl)-amino]-acetic acid; [(6-Benzyloxy-1-Chloro-4-hydroxy-isoquinoline-3-carbonyl)-methyl-amino]-acetic acid; [(1-Chloro-4-hydroxy-isoquinoline-3-carbonyl)-methyl-amino]-acetic acid; [(1-Chloro-4-hydroxy-6-isopropoxy-isoquinoline-3-carbonyl)-methyl-amino]-acetic acid; [(1-Chloro-4-hydroxy-7-isopropoxy-isoquinoline-3-carbonyl)-methyl-amino]-acetic acid; [Carboxymethyl-(1-Chloro-4-hydroxy-6isopropoxy-isoquinoline-3-carbonyl)-amino]-acetic acid; [Carboxymethyl-(1-Chloro-4-hydroxy-6-isopropoxy-isoquinoline-3-carbonyl)-amino]-acetic acid; 1-Chloro-4-hydroxy-isoquinoline-3-carboxylic acid (2-amino-ethyl)-amide (trifluoro-acetic acid salt); 1-Chloro-4-hydroxy-isoquinoline-3-carboxylic acid (2-methoxy-ethyl)-amide; 1-Chloro-4-hydroxy-isoquinoline-3-carboxylic acid (2-hydroxy-ethyl)-amide; 1-Chloro-4-hydroxy-isoquinoline-3-carboxylic acid (2-dimethylamino-ethyl)-amide; 1-Chloro-4-hydroxy-isoquinoline-3-carboxylic acid (2-acetylamino-ethyl)-amide; 1-Chloro-4-hydroxy-6-isopropoxy-isoquinoline-3-carboxylic acid (2-hydroxy-ethyl)-amide; 1-Chloro-4-hydroxy-6-isopropoxy-isoquinoline-3-carboxylic acid (2-methoxy-ethyl)-amide; 1-Chloro-4-hydroxy-6-isopropoxy-isoquinoline-3-carboxylic acid (2-amino-ethyl)-amide (trifluoro-acetic acid salt); 1-Chloro-4-hydroxy-6-isopropoxy-isoquinoline-3-carboxylic acid (2-dimethylamino-ethyl)-amide; 1-Chloro-4-hydroxy-7-isopropoxy-isoquinoline-3-carboxylic acid (2-amino-ethyl)-amide (trifluoro-acetic acid salt); 1-Chloro-4-hydroxy-7-isopropoxy-isoquinoline-3-carboxylic acid (2-methoxy-ethyl)-amide; 1-Chloro-4-hydroxy-7-isopropoxy-isoquinoline-3-carboxylic acid (2-dimethylamino-ethyl)-amide; 1-Chloro-4-hydroxy-7-isopropoxy-isoquinoline-3-carboxylic acid (2-hydroxy-ethyl)-amide; (S)-2-[(6-Benzyloxy-1-Chloro-4-hydroxy-isoquinoline-3-carbonyl)-amino]-propionic acid; (R)-2-[(1-Chloro-4-hydroxy-isoquinoline-3-carbonyl)-amino]-3-hydroxy-propionic acid; (S)-2-[(1-Chloro-4-hydroxy-isoquinoline-3-carbonyl)-amino]-3-hydroxy-propionic acid; (R)-2-[(1-Chloro-4-hydroxy-6-isopropoxy-isoquinoline-3-carbonyl)-amino]-3-hydroxy-propionic acid; (S)-2-[(1-Chloro-4-hydroxy-6-isopropoxy-isoquinoline-3-carbonyl)-amino]-3-hydroxy-propionic acid; (R)-2-[(1-Chloro-4-hydroxy-7-isopropoxy-isoquinoline-3-carbonyl)-amino]-3-hydroxy-propionic acid; (S)-2-[(1-Chloro-4-hydroxy-7-isopropoxy-isoquinoline-3-carbonyl)-amino]-3-hydroxy-propionic acid; 2-[(1-Chloro-4-hydroxy-isoquinoline-3-carbonyl)-amino]-2-methyl-propionic acid; 2-[(1-Chloro-4-hydroxy-6-isopropoxy-isoquinoline-3-carbonyl)-amino]-2-methyl-propionic acid; (R)-2-[(1-Chloro-4-hydroxy-isoquinoline-3-carbonyl)-amino]-3-(1H-imidazol-4-yl)-propionic acid (trifluoro-acetic acid salt); (S)-2-[(1-Chloro-4-hydroxy-isoquinoline-3-carbonyl)-amino]-3-(1H-imidazol-4-yl)-propionic acid (trifluoro-acetic acid salt); (R)-2-[(1-Chloro-4-hydroxy-isoquinoline-3-carbonyl)-amino]-3-methyl-butyric acid; (S)-2-[(1-Chloro-4-hydroxy-isoquinoline-3-carbonyl)-amino]-3-methyl-butyric acid; (R)-2-[(1-Chloro-4-hydroxy-6-isopropoxy-isoquinoline-3-carbonyl)-amino]-3-methyl-butyric acid; (S)-2-[(1-Chloro-4-hydroxy-6-isopropoxy-isoquinoline-3-carbonyl)-amino]-3-methyl-butyric acid; (R)-2-[(1-Chloro-4-hydroxy-7-isopropoxy-isoquinoline-3-carbonyl)-amino]-3-methyl-butyric acid; (S)-2-[(1-Chloro-4-hydroxy-7-isopropoxy-isoquinoline-3-carbonyl)-amino]-3-methyl-butyric acid; (S)-2-[(6-Benzyloxy-1-Chloro-4-hydroxy-isoquinoline-3-carbonyl)-amino]-3-methyl-butyric acid; (R)-2-[(1-Chloro-4-hydroxy-isoquinoline-3-carbonyl)-amino]-3-phenyl-propionic acid; (S)-2-[(1-Chloro-4-hydroxy-isoquinoline-3- carbonyl)-amino]-3-phenyl-propionic acid; (R)-2-[(1-Chloro-4-hydroxy-6-isopropoxy-isoquinoline-3-carbonyl)-amino]-3-phenyl-propionic acid; (S)-2-[(1-Chloro-4-hydroxy-6-isopropoxy-isoquinoline-3-carbonyl)-amino]-3-phenyl-propionic acid; (R)-2-[(1-Chloro-4-hydroxy-7-isopropoxy-isoquinoline-3-carbonyl)-amino]-3-phenyl-propionic acid; (S)-2-[(1-Chloro-4-hydroxy-7-isopropoxy-isoquinoline-3-carbonyl)-amino]-3-phenyl-propionic acid; (R)-2-[(1-Chloro-4-hydroxy-isoquinoline-3-carbonyl)-amino]-3-(4-hydroxy-phenyl)-propionic acid; (S)-2-[(1-Chloro-4-hydroxy-isoquinoline-3-carbonyl)-amino]-3-(4-hydroxy-phenyl)-propionic acid; (R)-2-[(1-Chloro-4-hydroxy-6-isopropoxy-isoquinoline-3-carbonyl)-amino]-3-(4-hydroxy-phenyl)-propionic acid; (S)-2-[(1-Chloro-4-hydroxy-6-isopropoxy-isoquinoline-3-carbonyl)-amino]-3-(4-hydroxy-phenyl)-propionic acid; (R)-2-[(1-Chloro-4-hydroxy-7-isopropoxy-isoquinoline-3-carbonyl)-amino]-3-(4-hydroxy-phenyl)-propionic acid; (S)-2-[(1-Chloro-4-hydroxy-7-isopropoxy-isoquinoline-3-carbonyl)-amino]-3-(4-hydroxy-phenyl)-propionic acid; (R)-2-[(1-Chloro-4-hydroxy-6-isopropoxy-isoquinoline-3-carbonyl)-amino]-pentanoic acid; (S)-2-[(1-Chloro-4-hydroxy-6-isopropoxy-isoquinoline-3-carbonyl)-amino]-pentanoic acid; (R)-1-(1-Chloro-4-hydroxy-isoquinoline-3-carbonyl)-pyrrolidine-2-carboxylic acid; (S)-1-(1-Chloro-4-hydroxy-isoquinoline-3-carbonyl)-pyrrolidine-2-carboxylic acid; (R)-1-(1-Chloro-4-hydroxy-6-isopropoxy-isoquinoline-3-carbonyl)-pyrrolidine-2-carboxylic acid; (S)-1-(1-Chloro-4-hydroxy-6-isopropoxy-isoquinoline-3-carbonyl)-pyrrolidine-2-carboxylic acid; (R)-6-Amino-2-[(1-chloro-4-hydroxy-isoquinoline-3-carbonyl)-amino]-hexanoic acid (trifluoro-acetic acid salt); (S)-6-Amino-2-[(1-chloro-4-hydroxy-isoquinoline-3-carbonyl)-amino]-hexanoic acid (trifluoro-acetic acid salt); (R)-6-Amino-2-[(1-Chloro-4-hydroxy-6-isopropoxy-isoquinoline-3-carbonyl)-amino]-hexanoic acid; trifluoroacetic acid salt; (S)-6-Amino-2-[(1-Chloro-4-hydroxy-6-isopropoxy-isoquinoline-3-carbonyl)-amino]-hexanoic acid (trifluoro-acetic acid salt); (R)-6-Amino-2-[(1-Chloro-4-hydroxy-7-isopropoxy-isoquinoline-3-carbonyl)-amino]-hexanoic acid; trifluoroacetic acid salt; (S)-6-Amino-2-[(1-chloro-4-hydroxy-7-isopropoxy-isoquinoline-3-carbonyl)-amino]-hexanoic acid (trifluoro-acetic acid salt); (R)-2-[(1-Chloro-4-hydroxy-isoquinoline-3-carbonyl)-amino]-succinic acid; (S)-2-[(1-Chloro-4-hydroxy-isoquinoline-3-carbonyl)-amino]-succinic acid; (R)-2-[(1-Chloro-4-hydroxy-6-isopropoxy-isoquinoline-3-carbonyl)-amino]-succinic acid; (S)-2-[(1-Chloro-4-hydroxy-6-isopropoxy-isoquinoline-3-carbonyl)-amino]-succinic acid; (R)-2-[(1-Chloro-4-hydroxy-7-isopropoxy-isoquinoline-3-carbonyl)-amino]-succinic acid; 1-[(1-Chloro-4-hydroxy-isoquinoline-3-carbonyl)-amino-cyclopropanecarboxylic acid; 1-[(1-Chloro-4-hydroxy-6-isopropoxy-isoquinoline-3-carbonyl)-amino]-cyclopropanecarboxylic acid; Dideutero-[(1-Chloro-4-hydroxy-isoquinoline-3-carbonyl)-amino]-acetic acid; (R)-2-[(6-Benzyloxy-1-Chloro-4-hydroxy-isoquinoline-3-carbonyl)-amino]-propionic acid; (S)-2-[(7-Benzyloxy-1-Chloro-4-hydroxy-isoquinoline-3-carbonyl)-amino]-propionic acid; (R)-2-[(7-Benzyloxy-1-Chloro-4-hydroxy-isoquinoline-3-carbonyl)-amino]-propionic acid; (S)-2-[(1-Chloro-4-hydroxy-isoquinoline-3-carbonyl)-amino]-propionic acid; (R)-2-[(1-Chloro-4-hydroxy-isoquinoline-3-carbonyl)-amino]-propionic acid; (S)-2-[(6-Isopropoxy-1-Chloro-4-hydroxy-isoquinoline-3-carbonyl)-amino]-propionic acid; (R)-2-[6-Isopropoxy-1-Chloro-4-hydroxy-isoquinoline-3-carbonyl)-amino]-propionic acid; (S)-2-[(7-Isopropoxy-1-Chloro-4-hydroxy-isoquinoline-3-carbonyl)-amino-propionic acid; (R)-2-[(7-Isopropoxy-1-Chloro-4-hydroxy-isoquinoline-3-carbonyl)-amino]propionic acid; 1-Chloro-4-hydroxy-6-isopropoxy-isoquinoline-3-carboxylic acid (2-hydroxy-1-hydroxymethyl-ethyl)-amide; 1-Chloro-4-hydroxy-7-isopropoxy-isoquinoline-3-carboxylic acid (2-hydroxy-1-hydroxymethyl-ethyl)-amide; 1-Chloro-4-hydroxy-isoquinoline-3-carboxylic acid (2-hydroxy-1-hydroxymethyl-ethyl)-amide; {[7-(3,5-Difluoro-phenoxy)-4-hydroxy-isoquinoline-3-carbonyl]-amino}-acetic acid; {[6-(3,5-Difluoro-phenoxy)-4-hydroxy-isoquinoline-3-carbonyl]-amino}-acetic acid; ({7-[4-(4-Fluoro-phenoxy)-phenoxy]4-hydroxy-isoquinoline-3-carbonyl}-amino)-acetic acid; ({6-[4-(4-Fluoro-phenoxy)-phenoxy]-4-hydroxy-isoquinoline-3-carbonyl}-amino)-acetic acid; {[7-(3-Chloro-4-fluoro-phenoxy)-4-hydroxy-isoquinoline-3-carbonyl]-amino}-acetic acid; {[6-(3-Chloro-4-fluoro-phenoxy)-4-hydroxy-isoquinoline-3-carbonyl]-amino}-acetic acid; (S)-2-{[7-(3-fluoro-5-methoxy-phenoxy)-4-hydroxy-isoquinoline-3-carbonyl]-amino}-propionic acid; 2-(S)-[(7-Cyclohexyloxy-4-hydroxy-isoquinoline-3-carbonyl)-amino]-propionic acid; 2-(S)-{[7-(4-Fluoro-phenoxy)-4-hydroxy-1-methyl-isoquinoline-3-carbonyl]-amino]-propionic acid; 2-(S)-{[7-(4-Fluoro-phenoxy)-4-hydroxy-isoquinoline-3-carbonyl]-amino}-acid; 2-(S)-[(4-Hydroxy-1-methyl-7-phenoxy-isoquinoline-3-carbonyl)-amino]-propionic acid; 2-(S)-[(4-Hydroxy-1-methyl-7-phenylsulfanyl-isoquinoline-3-carbonyl)-amino]-propionic acid; 2-(S)-{[4-Hydroxy-7-(4-trifluoromethyl-phenoxy)-isoquinoline-3-carbonyl]-amino}-propionic acid; {[7-(4-Chloro-phenoxy)-4-hydroxy-1-methyl-isoquinoline-3-carbonyl]-amino}-acetic acid; {[6-(4-Chloro-phenoxy)-1-methyl-isoquinoline-3-carbonyl]-amino}-acetic acid; {[7-(3,5-Difluoro-phenoxy)-4-hydroxy-1-methyl-isoquinoline-3-carbonyl]-amino}-acetic acid; {[4-Hydroxy-7-(4-methoxy-phenoxy)-1-methyl-isoquinoline-3-carbonyl]-amino-}-acetic acid; {[4-Hydroxy-6-(4-methoxy-phenoxy)-1-methyl-isoquinoline-3-carbonyl]-amino-}-acetic acid; [(6-Cyclohexyloxy-4-hydroxy-isoquinoline-3-carbonyl)-amino]-acetic acid; [(7-Cyclohexyloxy-4-hydroxy-isoquinoline-3-carbonyl)-amino]-acetic acid; [(7-Cyclohexyloxy-4-hydroxy-1-methyl-isoquinoline-3-carbonyl)-amino]-acetic acid; [(7-Cyclohexylsulfanyl-4-hydroxy-isoquinoline-3-carbonyl)-amino]-acetic acid; [(7-Cyclohexanesulfonyl-4-hydroxy-isoquinoline-3-carbonyl)-amino]-acetic acid; [(4-Hydroxy-1-isobutyl-isoquinoline-3-carbonyl)-amino]-acetic acid; [(4-Hydroxy-1-pyridin-2-yl-isoquinoline-3-carbonyl)-amino]-acetic acid; [(1-Ethyl-4-hydroxy-7-phenoxy-isoquinoline-3-carbonyl)-amino]-acetic acid; [(1-Dimethylaminomethyl-4-hydroxy-7-phenylsulfanyl-isoquinoline-3-carbonyl)-amino]-acetic acid; [(4-Hydroxy-1-methyl-7-phenylsulfanyl-isoquinoline-3-carbonyl)-amino]-acetic acid; and {[4-Hydroxy-1-methyl-7-(4-trifluoromethyl-phenoxy)-isoquinoline-3-carbonyl]-amino}-acetic acid.

In other embodiments, the agent is selected from the group consisting of: [(1-Chloro-4-hydroxy-isoquinoline-3-carbonyl)-amino]-acetic acid, [(4-Hydroxy-1-methyl-7-phenoxy-isoquinoline-3-carbonyl)-amino]-acetic acid, {[4-Hydroxy-7-(4-methoxy-phenoxy)-isoquinoline-3-carbonyl]-amino}-acetic acid, [(4-Hydroxy-8-phenoxy-isoquinoline-3-carbonyl)-amino]-acetic acid, [(4-Hydroxy-1-methyl-8-phenoxy-isoquinoline-3-carbonyl)-amino]-acetic acid, [(7-Chloro-4-hydroxy-1-methyl-isoquinoline-3-carbonyl)-amino]-acetic acid, {[8-(4-Fluoro-phenoxy)-4-hydroxy-1-methyl-isoquinoline-3-carbonyl]-amino}acetic acid, and [(4-cyano-7-hydroxy-thieno[3,2-c]pyridine-6-carbonyl)-amino]-acetic acid.

In particular embodiments, an agent for use in the present methods is Compound A ([(4-Hydroxy-7-phenylsulfanyl-isoquinoline-3-carbonyl)-amino]-acetic acid).

Exemplary compounds in the invention are also described in European Patent Nos. EP0650960 and EP0650961; U.S. Pat. Nos. 5,658,933; 5,620,995; 6,020,350; 5,607,954, 5,610, 172; 5,620,996; 5,719,164; 5,726,305; 6,093,730; and 7,323, 475; US Published Patent Applications 2007/0213335; 2007/0298104; 2008/0004309; 2006/0217416; and 2006/0199836; and International Publication No. WO 00/50390. All compounds listed in the above-patent and patent applications are hereby incorporated into the present application by reference herein.

Some agents useful in the instant methods are selective inhibitors of propyl hydroxylases. For instance, selective inhibitors of PHD-1, PHD-2, and PHD-3 are included within the methods of the invention. As shown in the data presented in the Examples it has been discovered that human tissue extracted from patients having ulcerative colitis or Crohns' disease express differential levels of PHD-1, PHD-2, and PHD-3. Decreases in all PHDs were observed in colonic tissue of patients with ulcerative colitis and significant decreases in particular of PHD-3 were observed in tissue of Crohns' disease patients.

Agents that inhibit HIF hydroxylase activity also include HIF hydroxylase expression inhibitors. A HIF hydroxylase expression inhibitor as used herein is molecule that knocks down expression of HIF hydroxylase. Thus, the invention also features the use of small nucleic acid molecules, referred to as short interfering nucleic acid (siNA) that include, for example: microRNA (miRNA), short interfering RNA (siRNA), double-stranded RNA (dsRNA), and short hairpin RNA (shRNA) molecules to knockdown expression of proteins such as HIF hydroxylase. An siNA of the invention can be unmodified or chemically-modified. An siNA of the instant invention can be chemically synthesized, expressed from a vector or enzymatically synthesized. The instant invention also features various chemically-modified synthetic short interfering nucleic acid (siNA) molecules capable of modulating gene expression or activity in cells by RNA interference (RNAi). The use of chemically-modified siNA improves various properties of native siNA molecules through, for example, increased resistance to nuclease degradation in vivo and/or through improved cellular uptake. Furthermore, siNA having multiple chemical modifications may retain its RNAi activity. The siNA molecules of the instant invention provide useful reagents and methods for a variety of therapeutic applications. In some embodiments the HIF hydroxylase expression inhibitors are used for treating inflammatory diseases other than IBD such as other inflammatory mucosal diseases including intestinal disease and skin disease.

Chemically synthesizing nucleic acid molecules with modifications (base, sugar and/or phosphate) that prevent their degradation by serum ribonucleases can increase their potency (see e.g., Eckstein et al., International Publication No. WO 92/07065; Perrault et al, 1990 Nature 344, 565; Pieken et al., 1991, Science 253, 314; Usman and Cedergren, 1992, Trends in Biochem. Sci. 17, 334; Usman et al., International Publication No. WO 93/15187; and Rossi et al., International Publication No. WO 91/03162; Sproat, U.S. Pat. No. 5,334,711; and Burgin et al., supra; all of these describe various chemical modifications that can be made to the base, phosphate and/or sugar moieties of the nucleic acid molecules herein). Modifications which enhance their efficacy in cells, and removal of bases from nucleic acid molecules to shorten oligonucleotide synthesis times and reduce chemical requirements are desired.

There are several examples in the art describing sugar, base and phosphate modifications that can be introduced into nucleic acid molecules with significant enhancement in their nuclease stability and efficacy. For example, oligonucleotides are modified to enhance stability and/or enhance biological activity by modification with nuclease resistant groups, for example, 2'amino, 2'-C-allyl, 2'-flouro, 2'-O-methyl, 2'-H, nucleotide base modifications (for a review see Usman and Cedergren, 1992, TIBS. 17, 34; Usman et al., 1994, Nucleic Acids Symp. Ser. 31, 163; Burgin et al., 1996, Biochemistry, 35, 14090). Sugar modification of nucleic acid molecules have been extensively described in the art (see Eckstein et al., International Publication PCT No. WO 92/07065; Perrault et al. Nature, 1990, 344, 565 568; Pieken et al. Science, 1991, 253, 314317; Usman and Cedergren, Trends in Biochem. Sci., 1992, 17, 334 339; Usman et al. International Publication PCT No. WO 93/15187; Sproat, U.S. Pat. No. 5,334,711 and Beigelman et al., 1995, J. Biol. Chem., 270, 25702; Beigelman et al., International PCT publication No. WO 97/26270; Beigelman et al., U.S. Pat. No. 5,716,824; Usman et al., molecule comprises one or more chemical modifications.

In one embodiment, one of the strands of the double-stranded siNA molecule comprises a nucleotide sequence that is complementary to a nucleotide sequence of a target RNA or a portion thereof, and the second strand of the double-stranded siNA molecule comprises a nucleotide sequence identical to the nucleotide sequence or a portion thereof of the targeted RNA. In another embodiment, one of the strands of the double-stranded siNA molecule comprises a nucleotide sequence that is substantially complementary to a nucleotide sequence of a target RNA or a portion thereof, and the second strand of the double-stranded siNA molecule comprises a nucleotide sequence substantially similar to the nucleotide sequence or a portion thereof of the target RNA. In another embodiment, each strand of the siNA molecule comprises about 19 to about 23 nucleotides, and each strand comprises at least about 19 nucleotides that are complementary to the nucleotides of the other strand.

In some embodiments an siNA is an shRNA, shRNA-mir, or microRNA molecule encoded by and expressed from a genomically integrated transgene or a plasmid-based expression vector. Thus, in some embodiments a molecule capable of inhibiting mRNA expression, or microRNA activity, is a transgene or plasmid-based expression vector that encodes a small-interfering nucleic acid. Such transgenes and expression vectors can employ either polymerase II or polymerase III promoters to drive expression of these shRNAs and result in functional siRNAs in cells. The former polymerase permits the use of classic protein expression strategies, including inducible and tissue-specific expression systems. In some embodiments, transgenes and expression vectors are controlled by tissue specific promoters. In other embodiments transgenes and expression vectors are controlled by inducible promoters, such as tetracycline inducible expression systems.

In another embodiment, a small interfering nucleic acid of the invention is expressed in mammalian cells using a mammalian expression vector. The recombinant mammalian expression vector may be capable of directing expression of the nucleic acid preferentially in a particular cell type (e.g., tissue-specific regulatory elements are used to express the nucleic acid). Tissue specific regulatory elements are known in the art. Non-limiting examples of suitable tissue-specific promoters include the myosin heavy chain promoter, albumin promoter, lymphoid-specific promoters, neuron specific promoters, pancreas specific promoters, and mammary gland specific promoters. Developmentally-regulated promoters are also encompassed, for example the murine hox promoters and the a-fetoprotein promoter.

Other inhibitor molecules that can be used include sense and antisense nucleic acids (single or double stranded), ribozymes, peptides, DNAzymes, peptide nucleic acids (PNAs), triple helix forming oligonucleotides, antibodies, and aptamers and modified form(s) thereof directed to sequences in gene(s), RNA transcripts, or proteins. Antisense and ribozyme suppression strategies have led to the reversal of a tumor phenotype by reducing expression of a gene product or by cleaving a mutant transcript at the site of the mutation (Carter and Lemoine Br. J. Cancer. 67(5):869-76, 1993; Lange et al., Leukemia. 6(11):1786-94, 1993; Valera et al., J. Biol. Chem. 269(46):28543-6, 1994; Dosaka-Akita et al., Am. J. Clin. Pathol. 102(5):660-4, 1994; Feng et al., Cancer Res. 55(10):2024-8, 1995; Quattrone et al., Cancer Res. 55(1):90-5, 1995; Lewin et al., Nat Med. 4(8):967-71, 1998). For example, neoplastic reversion was obtained using a ribozyme targeted to an H-Ras mutation in bladder carcinoma cells (Feng et al., Cancer Res. 55(10):2024-8, 1995). Ribozymes have also been proposed as a means of both inhibiting gene expression of a mutant gene and of correcting the mutant by targeted trans-splicing (Sullenger and Cech Nature 371(6498):619-22, 1994; Jones et al., Nat. Med. 2(6): 643-8, 1996). Ribozyme activity may be augmented by the use of, for example, non-specific nucleic acid binding proteins or facilitator oligonucleotides (Herschlag et al., Embo J. 13(12):2913-24, 1994; Jankowsky and Schwenzer Nucleic Acids Res. 24(3):423-9, 1996). Multitarget ribozymes (connected or shotgun) have been suggested as a means of improving efficiency of ribozymes for gene suppression (Ohkawa et al., Nucleic Acids Symp Ser. (29):121-2, 1993).

Anti-sense oligonucleotides may be designed to hybridize to the complementary sequence of nucleic acid, pre-mRNA or mature mRNA, interfering with the production of a HIF hydroxylase encoded by a given DNA sequence (e.g. either native polypeptide or a mutant form thereof), so that its expression is reduce or prevented altogether. Anti-sense techniques may be used to target a coding sequence; a control sequence of a gene, e.g. in the 5' flanking sequence, whereby the anti-sense oligonucleotides can interfere with control sequences. Anti-sense oligonucleotides may be DNA or RNA and may be of around 14-23 nucleotides, particularly around 15-18 nucleotides, in length. The construction of antisense sequences and their use is described in Peyman and Ulman, Chemical Reviews, 90:543-584, (1990), and Crooke, Ann. Rev. Pharmacol. Toxicol., 32:329-376, (1992).

It may be preferable that there is complete sequence identity in the sequence used for down-regulation of expression of a target sequence, and the target sequence, though total complementarity or similarity of sequence is not essential. One or more nucleotides may differ in the sequence used from the target gene. Thus, a sequence employed in a down-regulation of gene expression in accordance with the present invention may be a wild-type sequence (e.g. gene) selected from those available, or a mutant, derivative, variant or allele, by way of insertion, addition, deletion or substitution of one or more nucleotides, of such a sequence.

The sequence need not include an open reading frame or specify an RNA that would be translatable. It may be preferred for there to be sufficient homology for the respective sense RNA molecules to hybridize. There may be down regulation of gene expression even where there is about 5%, 10%, 15% or 20% or more mismatch between the sequence used and the target gene.

Triple helix approaches have also been investigated for sequence-specific gene suppression. Triple helix forming oligonucleotides have been found in some cases to bind in a sequence-specific manner (Postel et al., Proc. Natl. Acad. Sci. U.S.A. 88(18):8227-31, 1991; Duval-Valentin et al., Proc. Natl. Acad. Sci. U.S.A. 89(2):504-8, 1992; Hardenbol and Van Dyke Proc. Natl. Acad. Sci. U.S.A. 93(7):2811-6, 1996; Porumb et al., Cancer Res. 56(3):515-22, 1996). Similarly, peptide nucleic acids have been shown to inhibit gene expression (Hanvey et al., Antisense Res. Dev. 1(4):307-17, 1991; Knudsen and Nielson Nucleic Acids Res. 24(3):494-500, 1996; Taylor et al., Arch. Surg. 132(11):1177-83, 1997). Minor-groove binding polyamides can bind in a sequence-specific manner to DNA targets and hence may represent useful small molecules for future suppression at the DNA level (Trauger et al., Chem. Biol. 3(5):369-77, 1996). In addition, suppression has been obtained by interference at the protein level using dominant negative mutant peptides and antibodies (Herskowitz Nature 329(6136):219-22, 1987; Rimsky et al., Nature 341(6241):453-6, 1989; Wright et al., Proc. Natl. Acad. Sci. U.S.A. 86(9):3199-203, 1989). In some cases suppression strategies have led to a reduction in RNA levels without a concomitant reduction in proteins, whereas in others, reductions in RNA have been mirrored by reductions in protein.

The diverse array of suppression strategies that can be employed includes the use of DNA and/or RNA aptamers that can be selected to target, for example, a protein of interest such as HIF hydroxylase.

An example of a target for expression inhibitors is PHD-1, PHD-2, and PHD-3. Nucleotides sequences for each of PHD-1, PHD-2, and PHD-3 are known and thus interfering nucleic acids can be designed. PHD-1, also referred to as EGLN2 (egl nine homolog 2) is located on Chromosome: 19; Location: 19q13.2 having record number: NC_000019.8 (45996888 ... 46006177) and a Genbank ID No. of 112398. PHD-2, also referred to as EGLN1 (egl nine homolog 1) is located on Chromosome: 19; Location: 19q12 having record number: NC_005118.2 (55080746 ... 55118226, complement) and a Genbank ID No. of 308913 and 54583. PHD-3, also referred to as EGLN3 (egl nine homolog 3) is located on Chromosome 7; having record number: NC_007864.1 (96859279 ... 96895587, complement) and a Genbank ID No. of 71734.

Homologous recombination may be used to disrupt or mutate endogenous sequences in cells encoding HIF hydroxylases.

HIF agonists are HIF activators. An HIF activator as used herein a compound that produces active HIF in a cell. For instance HIF activators include but are not limited to compounds that stabilize HIF and exogenous HIF. Exogenous HIF is a HIF protein or a nucleic capable of expressing functional HIF in a cell.

HIF polypeptides (including whole proteins and partial proteins) such as those encoded by the HIF nucleic acids described herein may be delivered to a subject as a HIF pathway activator. HIF polypeptides are useful, for example, alone or as fusion proteins. HIF polypeptides can be isolated from biological samples including tissue or cell homogenates, and can also be expressed recombinantly in a variety of prokaryotic and eukaryotic expression systems by constructing an expression vector appropriate to the expression system, introducing the expression vector into the expression system, and isolating the recombinantly expressed protein. Fragments of the HIF polypeptides also can be synthesized chemically using well-established methods of peptide synthesis.

As used herein, a "variant" of a HIF polypeptide is a polypeptide which contains one or more modifications to the primary amino acid sequence of a HIF polypeptide. Modifications which create a HIF polypeptide variant can be made to a HIF polypeptide to enhance a property of a HIF polypeptide, such as protein stability or to provide a novel activity or property to a HIF polypeptide, such as addition of a detectable moiety.

Modifications to a HIF polypeptide are typically made to the nucleic acid which encodes the HIF polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the HIF polypeptide amino acid sequence. One of skill in the art will be familiar with methods for predicting the effect on protein conformation of a change in protein sequence, and can thus "design" a variant HIF polypeptide according to known methods. One example of such a method is described by Dahiyat and Mayo in Science 278:82-87, 1997, whereby proteins can be designed de novo. The method can be applied to a known protein to vary only a portion of the polypeptide sequence. By applying the computational methods of Dahiyat and Mayo, specific variants of a HIF polypeptide can be proposed and tested to determine whether the variant retains a desired conformation.

In general, variants include HIF polypeptides which are modified specifically to alter a feature of the polypeptide unrelated to its desired physiological activity. For example, cysteine residues can be substituted or deleted to prevent unwanted disulfide linkages. Similarly, certain amino acids can be changed to enhance expression of a HIF polypeptide by eliminating proteolysis by proteases in an expression system (e.g., dibasic amino acid residues in yeast expression systems in which KEX2 protease activity is present).

Mutations of a nucleic acid which encode a HIF polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

The skilled artisan will also realize that conservative amino acid substitutions may be made in HIF polypeptides to provide functionally equivalent variants, or homologs of the foregoing polypeptides, i.e., the variants retain the functional capabilities of the HIF polypeptides. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Exemplary functionally equivalent variants or homologs of the HIF polypeptides include conservative amino acid substitutions of in the amino acid sequences of proteins disclosed herein. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D. Therefore, one can make conservative amino acid substitutions to the amino acid sequence of the HIF polypeptides disclosed herein.

The nucleic acids and polypeptides of the invention are isolated nucleic acids and polypeptides. As used herein the term "isolated nucleic acid molecule" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid or polypeptide may be substantially purified, but need not be. For example, a nucleic acid that is isolated within a cloning or expression vector is not pure in that it may comprise only a small percentage of the material in the cell in which it resides. Such a nucleic acid is isolated, however, as the term is used herein because it is readily manipulable by standard techniques known to those of ordinary skill in the art.

The HIF nucleic acid molecules of the invention also encompass homologs and alleles which can be identified by conventional techniques. Identification of human and other organisms' homologs of HIF polypeptides will be familiar to those of skill in the art. In general, nucleic acid hybridization is a suitable method for identification of homologous sequences of another species (e.g., human, cow, sheep, dog, rat, mouse), which correspond to a known sequence. Standard nucleic acid hybridization procedures can be used to identify related nucleic acid sequences of selected percent identity. For example, one can construct a library of cDNAs reverse transcribed from the mRNA of a selected tissue and use the HIF nucleic acid molecules identified herein to screen the library for related nucleotide sequences. The screening preferably is performed using high-stringency conditions to identify those sequences that are closely related by sequence identity. Nucleic acids so identified can be translated into polypeptides and the polypeptides can be tested for activity.

The term "high stringency" as used herein refers to parameters with which the art is familiar. Nucleic acid hybridization parameters may be found in references that compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. More specifically, high-stringency conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$ (pH7), 0.5% SDS, 2 mM EDTA). SSC is 0.15M sodium chloride/0.015M sodium citrate, pH7; SDS is sodium dodecyl sulphate; and EDTA is ethylenediaminetetracetic acid. After hybridization, the membrane upon which the DNA is transferred is washed, for example, in 2×SSC at room temperature and then at 0.1-0.5× SSC/0.1×SDS at temperatures up to 68° C.

There are other conditions, reagents, and so forth that can be used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of the HIF nucleic acids of the invention (e.g., by using lower stringency conditions). The skilled artisan also is familiar with the methodology for screening cells and libraries for expression of such molecules, which then are routinely isolated, followed by isolation of the pertinent nucleic acid molecule and sequencing.

In general, homologs and alleles typically will share at least 90% nucleotide identity and/or amino acid identity to the sequences of HIF nucleic acids and polypeptides, respectively, in some instances will share at least 95% nucleotide identity and/or amino acid identity, in other instances will share at least 97% nucleotide identity and/or amino acid identity, in other instances will share at least 98% nucleotide identity and/or amino acid identity, and in other instances will share at least 99% nucleotide identity and/or amino acid identity. The homology can be calculated using various, publicly available software tools developed by NCBI (Bethesda, Md.) that can be obtained through the interne. Exemplary tools include the BLAST system available from the website of the National Center for Biotechnology Information (NCBI) at the National Institutes of Health. Pairwise and ClustalW alignments (BLOSUM30 matrix setting) as well as Kyte-Doolittle hydropathic analysis can be obtained using a number of sequence analysis software programs, such as the MacVector sequence analysis software (Accelrys Software Inc., San Diego, Calif.). Watson-Crick complements of the foregoing nucleic acids also are embraced by the invention.

The invention also includes degenerate nucleic acids that include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating HIF polypeptide. Similarly, nucleotide sequence triplets which encode other amino acid residues include, but are not limited to: CCA, CCC, CCG, and CCT (proline codons); CGA, CGC, CGG, CGT, AGA, and AGG (arginine codons); ACA, ACC, ACG, and ACT (threonine codons); AAC and AAT (asparagine codons); and ATA, ATC, and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides modified nucleic acid molecules, which include additions, substitutions and deletions of one or more nucleotides (preferably 1-20 nucleotides). In preferred embodiments, these modified nucleic acid molecules and/or the polypeptides they encode retain at least one activity or function of the unmodified nucleic acid molecule and/or the polypeptides, such as the ability to induce the expression of HIF specific genes. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art.

For example, modified nucleic acid molecules that encode polypeptides having single amino acid changes can be prepared. Each of these nucleic acid molecules can have one, two or three nucleotide substitutions exclusive of nucleotide changes corresponding to the degeneracy of the genetic code as described herein. Likewise, modified nucleic acid molecules that encode polypeptides having two amino acid changes can be prepared which have, e.g., 2-6 nucleotide changes.

An expression vector comprising the isolated HIF nucleic acid molecules of the invention, preferably operably linked to a promoter is used to deliver the nucleic acids to the cells of a subject. As used herein, a "vector" may be any of a number of nucleic acid molecules into which a desired sequence may be inserted by restriction and ligation for transport between different genetic environments or for expression in a host cell. Vectors are typically composed of DNA although RNA vectors are also available. Vectors include, but are not limited to, plasmids, phagemids, and virus genomes.

A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript.

Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art, e.g., β-galactosidase or alkaline phosphatase, and genes which visibly affect the phenotype of transformed or transfected cells, hosts, colonies or plaques, e.g., green fluorescent protein. Preferred vectors are those capable of autonomous replication and expression of the structural gene products present in the DNA segments to which they are operably joined.

As used herein, a coding sequence and regulatory sequences are said to be "operably joined" when they are covalently linked in such a way as to place the expression or transcription of the coding sequence under the influence or control of the regulatory sequences. As used herein, "operably joined" and "operably linked" are used interchangeably and should be construed to have the same meaning. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frameshift mutation, (2) interfere with the ability of the promoter region to direct the transcription of the coding sequences, or (3) interfere with the ability of the corresponding RNA transcript to be translated into a protein. Thus, a promoter region is operably joined to a coding sequence if the promoter region is capable of effecting transcription of that DNA sequence such that the resulting transcript can be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Often, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

In some embodiments the HIF pathway activator is one that has not previously been indicated for the treatment of an inflammatory bowel disease. A "HIF pathway activator is one that has not previously been indicated for the treatment of an inflammatory bowel disease" as used herein refers to a compound that had not, prior to the invention, been proposed for the treatment of the disease for which it is now, based on the discoveries of the invention, being used. For instance, a drug which had previously been proposed for the treatment of IBD would not fall within the scope of this particular embodiment even if it is a HIF pathway activator.

The invention is applicable to a variety of different organisms, including for example, vertebrates, large animals, and primates. In certain embodiments, the subject is a mammalian subject and, in particular embodiments, the subject is a human subject. Although medical applications with humans are clearly foreseen, veterinary applications are also envisaged here. Thus subjects include non-human primate, cow, horse, pig, sheep, goat, dog, cat or rodent. In all embodiments, human subjects are preferred.

It is contemplated in specific embodiments of the present invention that the present methods are directed to treating IBD or to reducing or ameliorating one or more symptoms of IBD in a subject in need, wherein the subject has or is at risk for having IBD. In certain embodiments, the subject has ulcerative colitis. In other embodiments, the subject has Crohn's disease. In further embodiments, the subject has diversion colitis, ischemic colitis, infectious colitis, chemical colitis, microscopic colitis (including collagenous colitis and lymphocytic colitis), atypical colitis, pseudomembranous colitis, fulminant colitis, autistic enterocolitis, indeterminate colitis, Behçet's disease, gastroduodenal Crohn's disease, jejunoileitis, ileitis, ileocolitis, or Crohn's (granulomatous) colitis.

The subject can be a subject having IBD of any etiology and with any level or degree of disease activity, including a subject with mild disease activity, with moderate disease activity, or with severe disease activity. It is further contemplated that in certain embodiments, the subject is a subject having one or more symptoms of IBD, including, but not limited to, a subject having abdominal pain and cramping, diarrhea (including bloody diarrhea), rectal bleeding, fever, weight loss, fatigue, loss of appetite, loss of bodily fluids (dehydration) and nutrients, anemia due to intestinal bleeding, or ulcers (including ulcers occurring anywhere along the length of the intestines or rectum).

As used herein, the term "treating" and "treatment" refers to modulating tissue particularly mucosal surfaces involving epithelial cells so that the subject has an improvement in the disease, for example, beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. One of skill in the art realizes that a treatment may improve the disease condition, but may not be a complete cure for the disease.

The active agents of the invention are administered to the subject in an effective amount for treating disorders such as inflammatory bowel disease. An "effective amount", for instance, is an amount necessary or sufficient to realize a desired biologic effect. An "effective amount for treating inflammatory bowel disease", for instance, could be that amount necessary to (i) prevent further physiological characteristics associated with inflammatory bowel disease such as increased intestinal permeability, colon length, structural alterations of the colon and/or (ii) arresting or slowing such physiological characteristics in the absence of the therapy. According to some aspects of the invention, an effective amount is that amount of a compound of the invention alone or in combination with another medicament, which when combined or co-administered or administered alone, results in a therapeutic response to the disease, either in the prevention or the treatment of the disease. The biological effect may be the amelioration and or absolute elimination of symptoms resulting from the disease. In another embodiment, the biological effect is the complete abrogation of the disease, as evidenced for example, by the absence of a symptom of the disease.

The effective amount of a compound of the invention in the treatment of a disease described herein may vary depending upon the specific compound used, the mode of delivery of the compound, and whether it is used alone or in combination. The effective amount for any particular application can also vary depending on such factors as the disease being treated, the particular compound being administered, the size of the subject, or the severity of the disease or condition. One of ordinary skill in the art can empirically determine the effective amount of a particular molecule of the invention without necessitating undue experimentation. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject.

Pharmaceutical compositions of the present invention comprise an effective amount of one or more agents, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences (1990), incorporated herein by reference). Except insofar as any conventional carrier is incompatible with the active ingredient, its use in the therapeutic or pharmaceutical compositions is contemplated.

The agent may comprise different types of carriers depending on whether it is to be administered in solid, liquid or aerosol form, and whether it need to be sterile for such routes of administration as injection. The present invention can be administered intravenously, intradermally, intraarterially, intralesionally, intratumorally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in creams, in lipid compositions (e.g., liposomes), or by other method or any combination of the forgoing as would be known to one of ordinary skill in the art (see, for example, Remington's Pharmaceutical Sciences (1990), incorporated herein by reference). In a particular embodiment, intraperitoneal injection is contemplated.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein.

A therapeutically effective dose or amount of a compound, agent, or drug of the present invention refers to an amount or dose of the compound, agent, or drug that results in a reduction or amelioration of symptoms, inhibition of further symptoms or a prolongation of survival in a subject. Toxicity and therapeutic efficacy of such molecules can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is the therapeutic index, which can be expressed as the ratio LD50/ED50. Agents that exhibit high therapeutic indices are preferred.

The effective amount or therapeutically effective amount is the amount of the compound or pharmaceutical composition that will elicit the biological or medical response of a tissue, system, animal, or human that is being sought by the researcher, veterinarian, medical doctor, or other clinician, e.g., treatment of IBD, reduction or amelioration of one or more symptoms of IBD, etc. Dosages preferably fall within a range of circulating concentrations that includes the ED50 with little or no toxicity. Dosages may vary within this range depending upon the dosage form employed and/or the route of administration utilized. The exact formulation, route of administration, dosage, and dosage interval should be chosen according to methods known in the art, in view of the specifics of a subject's condition. Dosage amount and interval may be adjusted individually to provide plasma levels of the active moiety that are sufficient to achieve the desired effects, i.e., minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

Subject doses of the compounds described herein typically range from about 0.1 µg to 10,000 mg, more typically from about 1 µg/day to 8000 mg, and most typically from about 10 µg to 100 µg. Stated in terms of subject body weight, typical dosages range from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. The absolute amount will depend upon a variety of factors including the concurrent treatment, the number of doses and the individual patient parameters including age, physical condition, size and weight. These are factors well known to those of ordinary skill in the art and can be addressed with no more than routine experimentation. It is preferred generally that a maximum dose be used, that is, the highest safe dose according to sound medical judgment.

Multiple doses of the molecules of the invention are also contemplated. In some instances, when the molecules of the invention are administered with another medicament, such as an anti-IBD agent, a sub-therapeutic dosage of either the molecules or a sub-therapeutic dosage of both, is used in the treatment of a subject having, or at risk of developing an inflammatory bowel disease. When the two classes of drugs are used together, the anti-IBD agent may be administered in a sub-therapeutic dose to produce a desirable therapeutic result. A "sub-therapeutic dose" as used herein refers to a dosage which is less than that dosage which would produce a therapeutic result in the subject if administered in the absence of the other agent. Thus, the sub-therapeutic dose of an anti-IBD agent is one which would not produce the desired therapeutic result in the subject in the absence of the administration of the molecules of the invention. Therapeutic doses of anti-IBD agents are well known in the field of medicine. These dosages have been extensively described in references such as Remington's Pharmaceutical Sciences, 18th ed., 1990; as well as many other medical references relied upon by the medical profession as guidance for the treatment of inflammatory bowel disease. Other anti-IBD agents therapeutic agents useful for administration in combination with agents of the present invention include anti-inflammatory agents (e.g., mesalamine, sulfasalazine, infliximab, adalimumab, prednisone, budesonide) and immunosuppressive agents (e.g., 6-mercaptopurine, azathioprine, cyclosporine). The administration of one or more anti-inflammatory agents and/or one or more immunosuppressive agents in combination with one or more agents of the present invention may be simultaneous, separate, or sequential administration, and administration may be in any order. In additional embodiments, effective treatment regimes for compounds of the invention include administration once weekly, two times weekly, three times weekly, or more than three times weekly.

In any case, the composition may comprise various antioxidants to retard oxidation of one or more components. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The agent may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups also can be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

The compounds of the invention can be administered by any ordinary route for administering medications. The particular mode selected will depend, of course, upon the particular active agents selected, the particular condition being treated and the dosage required for therapeutic efficacy. The methods of this invention, generally speaking, may be practiced using any mode of administration that is medically acceptable, meaning any mode that produces effective levels of protection without causing clinically unacceptable adverse effects. Preferred routes of administration include but are not limited to oral, parenteral, intramuscular, intranasal, intratracheal, intrathecal, intravenous, inhalation, ocular, dermal, sublingual, vaginal, and rectal. For use in therapy, an effective amount of the compounds of the invention can be administered to a subject by any mode that delivers the active compound to the affected organ or tissue. "Administering" the pharmaceutical composition of the present invention may be accomplished by any means known to the skilled artisan.

According to the methods of the invention, the compound may be administered in a pharmaceutical composition. In general, a pharmaceutical composition comprises the compound of the invention and a pharmaceutically-acceptable carrier. Pharmaceutically-acceptable carriers for small molecules, nucleic acids, peptides, monoclonal antibodies, and antibody fragments are well-known to those of ordinary skill in the art. As used herein, a pharmaceutically-acceptable carrier means a non-toxic material that does not interfere with the effectiveness of the biological activity of the active ingredients.

Pharmaceutically acceptable carriers include diluents, fillers, salts, buffers, stabilizers, solubilizers and other materials which are well-known in the art. Exemplary pharmaceutically acceptable carriers for peptides in particular are described in U.S. Pat. No. 5,211,657. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The compounds of the invention may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants.

Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

When the compounds described herein (including peptide and non-peptide varieties) are used therapeutically, in certain embodiments a desirable route of administration may be by pulmonary aerosol. Techniques for preparing aerosol delivery systems containing compounds are well known to those of skill in the art. Generally, such systems should utilize components which will not significantly impair the biological properties of the peptides (see, for example, Sciarra and Cutie, "Aerosols," in *Remington's Pharmaceutical Sciences*, 18th edition, 1990, pp 1694-1712; incorporated by reference). Those of skill in the art can readily determine the various parameters and conditions for producing aerosols without resort to undue experimentation.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. Several types of metered dose inhalers are regularly used for administration by inhalation. These types of devices include metered dose inhalers (MDI), breath-actuated MDI, dry powder inhaler (DPI), spacer/holding chambers in combination with MDI, and nebulizers. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. Techniques for preparing aerosol delivery systems are well known to those of skill in the art. Generally, such systems should utilize components which will not significantly impair the biological properties of the active agent (see, for example, Sciarra and Cutie, "Aerosols," in Remington's Pharmaceutical Sciences, 18th edition, 1990, pp 1694-1712; incorporated by reference). Those of skill in the art can readily determine the various parameters and conditions for producing aerosols without resort to undue experimentation.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of the active agent. Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated.

Formulations suitable for use with a nebulizer, either jet or ultrasonic, will typically comprise active agent dissolved in water at a concentration of about 0.1 to 25 mg of biologically active agent per mL of solution. The formulation may also include a buffer and a simple sugar. The nebulizer formulation may also contain a surfactant, to reduce or prevent surface induced aggregation of the active agent caused by atomization of the solution in forming the aerosol.

Formulations for use with a metered-dose inhaler device will generally comprise a finely divided powder containing the active agent suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing active agent and may also include a bulking agent, such as lactose, sorbitol, sucrose, or mannitol in amounts which facilitate dispersal of the powder from the device, e.g., 50 to 90% by weight of the formulation. The active agent should most advantageously be prepared in particulate form with an average particle size of less than 10 mm (or microns), most preferably 0.5 to 5 mm, for most effective delivery to the distal lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds of the invention may be administered directly to a tissue. Direct tissue administration may be achieved by direct injection, surgical application, topical application etc. The compounds may be administered once, or alternatively they may be administered in a plurality of administrations. If administered multiple times, the compounds may be administered via different routes. For example, the first (or the first few) administrations may be made directly into the affected tissue while later administrations may be systemic.

The term "topical administration" is used in its conventional sense to mean delivery of a topical drug or pharmacologically active agent to a body surface such as the skin or mucosa. The pharmaceutical formulations of the invention may contain a pharmaceutically acceptable topical carrier. The formulation may be in any form suitable for application to the body surface, and may comprise, for example, a cream, lotion, solution, gel, ointment, paste, powders, sprays and patches and/or may be prepared so as to contain carriers and delivery enhancers such as liposomes, micelles, and/or microspheres. The formulation may be aqueous, i.e., contain water, or may be nonaqueous and optionally used in combination with an occlusive overlayer so that moisture evaporating from the body surface is maintained within the formulation upon application to the body surface.

Ointments, as is well known in the art of pharmaceutical formulation, are semisolid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in Remington: The Science and Practice of Pharmacy, 19th Ed. (Easton, Pa.: Mack Publishing Co., 1995), at pages 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin, and hydrophilic petrolatum. Emulsion ointment bases are either water-in-oil (W/O) emulsions or oil-in-water (O/W) emulsions, and include, for example, cetyl alcohol, glyceryl monostearate, lanolin, and stearic acid.

Creams are viscous liquids or semisolid emulsions, either oil-in-water or water-in-oil. Cream bases are water-washable, and contain an oil phase, an emulsifier, and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic, or amphoteric surfactant.

Gels are semisolid, suspension-type systems. Single-phase gels contain organic macromolecules distributed substantially uniformly throughout the carrier liquid, which is typically aqueous, but also, preferably, contains an alcohol and, optionally, an oil. Preferred "organic macromolecules," i.e., gelling agents, are crosslinked acrylic acid polymers such as the "carbomer" family of polymers, e.g., carboxypolyalkylenes that may be obtained commercially under the Carbopol®. Also preferred are hydrophilic polymers such as polyethylene oxides, polyoxyethylene-polyoxypropylene copolymers, and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing, or stirring, or combinations thereof.

Lotions are preparations to be applied to the skin or mucosa surface without friction, and are typically liquid or semiliquid preparations in which solid particles, including the active agent, are present in a water or alcohol base. Lotions are usually suspensions of solids, and preferably, for the present purpose, comprise a liquid oily emulsion of the oil-in-water type. Lotions are preferred formulations herein for treating large body areas, because of the ease of applying a more fluid composition. Generally necessary that the insoluble matter in a lotion is finely divided. Lotions will typically contain suspending agents to produce better dispersions as well as compounds useful for localizing and holding the active agent in contact with the skin, e.g., methylcellulose, sodium carboxymethylcellulose, or the like.

Pastes are semisolid dosage forms in which the active agent is suspended in a suitable base. Depending on the nature of the base, pastes are divided between fatty pastes or those made from a single-phase aqueous gels. The base in a fatty paste is generally petrolatum, hydrophilic petrolatum, or the like. The pastes made from single-phase aqueous gels generally incorporate carboxymethylcellulose or the like as a base.

Powders may be formed with the aid of any suitable powder base, e.g., talc, lactose, starch, and the like. Drops may be formulated with an aqueous base or non-aqueous base also comprising one or more dispersing agents, suspending agents, solubilizing agents, and the like.

The ointments, pastes, creams and gels also may contain excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays also can contain excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Formulations may also be prepared with liposomes, micelles, and microspheres. Liposomes are microscopic vesicles having a lipid wall comprising a lipid bilayer, and can be used as drug delivery systems. Generally, liposome formulations are preferred for poorly soluble or insoluble pharmaceutical agents. Liposomal preparations for use in the instant invention include cationic (positively charged), anionic (negatively charged), and neutral preparations. Cationic liposomes are readily available. For example, N[1-2,3-dioleyloxy)propyl]-N,N,N-triethylammonium (DOTMA) liposomes are available under the tradename Lipofectin® (GIBCO BRL, Grand Island, N.Y.). Similarly, anionic and neutral liposomes are readily available as well, e.g., from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), and dioleoylphoshatidyl ethanolamine (DOPE), among others. These materials can also be mixed with DOTMA in appropriate ratios.

Micelles are surfactant molecules arranged so that their polar head groups form an outer spherical shell, while their hydrophobic, hydrocarbon chains are oriented towards the center of the sphere, forming a core. Micelles form in an aqueous solution containing surfactant at a high enough concentration so that micelles naturally result. Surfactants useful for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethylammonium chloride, dodecylammonium chloride, polyoxyl 8 dodecyl ether, polyoxyl 12 dodecyl ether, nonoxynol 10, and nonoxynol 30. Micelle formulations can be incorporated into a formulation to be applied to the body surface.

Microspheres, similarly, may be incorporated into the present formulations and drug delivery systems. Like liposomes and micelles, microspheres essentially encapsulate a drug or drug-containing formulation. Microspheres are generally, although not necessarily, formed from synthetic or naturally occurring biocompatible polymers, but may also be comprised of charged lipids such as phospholipids.

A variety of other additives may also be included in topical compositions. Ingredients for enhancing or providing humectant properties, spreadability, non-greasiness, fragrance, absorbability and many other desirable attributes of the novel skin treatment compositions can also be included. Any such additive ingredients are preferably selected to be without deleterious effect on the particular active agents used and their stability within the particular topical compositions.

It may be desirable, in some instances to include an added permeation enhancer in the formulation. Examples of suitable enhancers include, but are not limited to, ethers such as diethylene glycol monoethyl ether (available commercially as Transcutol®) and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80), and lecithin (U.S. Pat. No. 4,783,450); alcohols such as ethanol, propanol, octanol, benzyl alcohol, and the like; polyethylene glycol and esters thereof such as polyethylene glycol monolaurate (PEGML; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, ethanolamine, diethanolamine, and triethanolamine; terpenes; alkanones; and organic acids, particularly citric acid and succinic acid. Azone® and sulfoxides such as DMSO and $C_{10}$ MSO may also be used.

Enhancers include those lipophilic co-enhancers typically referred to as "plasticizing" enhancers, i.e., enhancers that have a molecular weight in the range of about 150 to 1000, and an aqueous solubility of less than about 1 wt. %, preferably less than about 0.5 wt. %, and most preferably less than about 0.2 wt. %. The Hildebrand solubility parameter of plasticizing enhancers is in the range of about 2.5 to about 10, preferably in the range of about 5 to about 10. Such enhancers are described in detail in co-pending, commonly assigned U.S. patent application Ser. No. 09/738,410, filed on Dec. 14, 2000, and in International Patent Application No. PCT/US00/34483, published Jun. 21, 2001 as WO 01/43775 A2. Preferred lipophilic enhancers are fatty esters, fatty alcohols, and fatty ethers. Examples of specific and most preferred fatty acid esters include methyl laurate, ethyl oleate, propylene glycol monolaurate, propylene glycerol dilaurate, glycerol monolaurate, glycerol monooleate, isopropyl n-decanoate, and octyldodecyl myristate. Fatty alcohols include, for example, stearyl alcohol and oleyl alcohol, while fatty ethers include compounds wherein a diol or triol, preferably a $C_2$-$C_4$ alkane diol or triol, is substituted with one or two fatty ether substituents.

Additional permeation enhancers will be known to those of ordinary skill in the art of topical drug delivery, and/or are described in the pertinent texts and literature.

The formulations may also contain irritation-mitigating additives to minimize or eliminate the possibility of skin or mucosal irritation or damage resulting from the pharmacologically active base or other components of the composition. Suitable irritation-mitigating additives include, for example: α-tocopherol; monoamine oxidase inhibitors, particularly phenyl alcohols such as 2-phenyl-1-ethanol; glycerin; salicylic acids and salicylates; ascorbic acids and ascorbates; ionophores such as monensin; amphiphilic amines; ammonium chloride; N-acetylcysteine; cis-urocanic acid; capsaicin; and chloroquine. The irritant-mitigating additive, if present, may be incorporated into the present formulations at a concentration effective to mitigate irritation or skin damage, typically representing not more than about 20 wt. %, more typically not more than about 5 wt. %, of the composition.

The compositions of the invention may also be applied to bandages, wound dressings, covers, or other membranes, which may or may not be waterproof. Examples of such membranes include, but are not limited to, semipermeable polyolefin (e.g., EXAIRE supplied by Tredegar Corporation, Richmond, Va., USA), expanded polytetrafluoroethylene (e.g., GORE-TEX supplied by W.L. Gore & Associates, Elkton, Md., USA), polyurethane foam (e.g., FLEXZAN supplied by Dow Hickam Pharmaceuticals, Sugar Land, Tex., USA), silicone and polytetrafluoroethylene (e.g., SILON-TSR, supplied by Bio Med Sciences, Allentown, Pa., USA), or the like.

For buccal administration, the compositions may take the form of tablets or lozenges formulated in conventional manner.

In some embodiments, the compounds of the invention are mixed with polyethylene glycol (e.g., PEG 1000) and administered to a subject via an enema. The enema may contain from about 0.0001 mg/kg to about 10 mg/kg of the active agents per kilogram weight of the subject administered the enema, although lower and higher concentrations are contemplated.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

The compounds may also be formulated in rectal or vaginal compositions such as suppositories or retention enemas, e.g., containing conventional suppository bases such as cocoa butter or other glycerides. Suppositories are a solid dosage form of medication that can be delivered internally to a patient, human or animal by insertion of the solid dosage form directly to the an area of the body. Known types of suppositories include rectal, vaginal and urethral suppositories. Commonly used bases, which are commercially available for suppositories include PCCA Base MBK™ (Fatty Acid Base, PCCA), PCCA Base A™ (Polyglycol 1450 MW, NF, PCCA), PCCA Base F™ (Synthetic Cocoa Butter, PCCA), Wecobee® M, R, S, W (Vegetable Oil, Hydrogenated, tepan Company, Northfield, Ill.), Witepsol® H12, H15, W35 (Vegetable Oil, Hydrogenated), Hydrokote® M (Vegetable Oil, Hydrogenated, Abitec Corporation, Columbus, Ohio), COA Base (Fatty Acid Base, Spectrum Pharmacy Products, Tucson), Supposibase (PEG/Vegetable, Spectrum Pharmacy Products, Tucson), Base A, B, D, Polyethylene Glycols, Spectrum Pharmacy Products, Tucson), and Polybase (Polyethylene Glycol Blend, Gallipot, Inc., St. Paul, Minn.)

In yet other embodiments, the preferred vehicle is a biocompatible microparticle or implant that is suitable for implantation into the mammalian recipient. Exemplary bioerodible implants that are useful in accordance with this method are described in PCT International Application No. PCT/US/03307 (Publication No. WO 95/24929, entitled "Polymeric Gene Delivery System", claiming priority to U.S. patent application Ser. No. 213,668, filed Mar. 15, 1994). PCT/US/0307 describes a biocompatible, preferably biodegradable polymeric matrix for containing a biological macromolecule. The polymeric matrix may be used to achieve sustained release of the agent in a subject. In accordance with one aspect of the instant invention, the agent described herein may be encapsulated or dispersed within the biocompatible, preferably biodegradable polymeric matrix disclosed in PCT/US/03307. The polymeric matrix preferably is in the form of a microparticle such as a microsphere (wherein the agent is dispersed throughout a solid polymeric matrix) or a microcapsule (wherein the agent is stored in the core of a polymeric shell). Other forms of the polymeric matrix for containing the agent include films, coatings, gels, implants, and stents. The size and composition of the polymeric matrix device is selected to result in favorable release kinetics in the tissue into which the matrix device is implanted. The size of the polymeric matrix device further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the device is administered to a vascular, pulmonary, or other surface. The matrix composition also can be selected not to degrade, but rather, to release by diffusion over an extended period of time.

Both non-biodegradable and biodegradable polymeric matrices can be used to deliver the agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

In general, the agents of the invention may be delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly (octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly (ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Other delivery systems can include time-release, delayed release or sustained release delivery systems. Such systems can avoid repeated administrations of the compound, increasing convenience to the subject and the physician. Many types of release delivery systems are available and known to those of ordinary skill in the art. They include polymer based systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the platelet reducing agent is contained in a form within a matrix such as those described in U.S. Pat. Nos. 4,452,775, 4,675,189, and 5,736,152 and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for treatment of chronic diseases. Long-term release, as used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

Therapeutic formulations useful in the invention may be prepared for storage by mixing a peptide or other molecule having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The agents described herein may, in some embodiments, be assembled into pharmaceutical or diagnostic or research kits to facilitate their use in therapeutic, diagnostic or research applications. A kit may include one or more containers housing the components of the invention and instructions for use. Specifically, such kits may include one or more agents described herein, along with instructions describing the intended therapeutic application and the proper administration of these agents. In certain embodiments agents in a kit may be in a pharmaceutical formulation and dosage suitable for a particular application and for a method of administration of the agents.

The kit may be designed to facilitate use of the methods described herein by physicians and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for human administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. The kit may have one or more or all of the components required to administer the agents to a patient, such as a syringe, topical application devices, or iv needle tubing and bag.

The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

Methods for identifying compounds and agents of the invention are also provided. Assays for hydroxylase activity are standard in the art. Such assays can directly or indirectly measure hydroxylase activity. For example, an assay can measure hydroxylated residues, e.g., proline, asparagine, etc., present in the enzyme substrate, e.g., a target protein, a synthetic peptide mimetic, or a fragment thereof. (See, e.g., Palmerini et al. (1985) J Chromatogr 339:285-292.) A reduction in hydroxylated residue, e.g., proline or asparagine, in the presence of a compound is indicative of a compound that inhibits hydroxylase activity. Alternatively, assays can measure other products of the hydroxylation reaction, e.g., formation of succinate from 2-oxoglutarate. (See, e.g., Cunliffe et al. (1986) Biochem J 240:617-619.) Kaule and Gunzler (1990 Anal Biochem 184:291-297) describe an exemplary procedure that measures production of succinate from 2-oxoglutarate.

Procedures such as those described above can be used to identify compounds that modulate HIF hydroxylase activity. Target proteins may include HIFα or a fragment thereof, e.g., HIF(556-575). Enzymes may include, e.g., HIF prolyl hydroxylase (see, e.g., GenBank Accession No. AAG33965, etc.) or HIF asparaginyl hydroxylase (see, e.g., GenBank Accession No. AAL27308, etc.), obtained from any source. Enzyme may also be present in a crude cell lysate or in a partially purified form. For example, procedures that measure HIF hydroxylase activity are described in Ivan et al. (2001, Science 292:464-468; and 2002, Proc Natl Acad Sci USA 99:13459-13464) and Hirsila et al. (2003, J Biol Chem 278:

30772-30780); additional methods are described in International Publication No. WO 03/049686. Measuring and comparing enzyme activity in the absence and presence of the compound will identify compounds that inhibit hydroxylation of HIFα.

A wide variety of assays for pharmacological agents can be used in accordance with this aspect of the invention, including, labeled in vitro protein-protein binding assays, electrophoretic mobility shift assays, immunoassays, kinase assays, cell-based assays such as two- or three-hybrid screens, expression assays, etc. Some exemplary assays are provided in the Examples below. The assay mixture comprises a candidate pharmacological agent. Typically, a plurality of assay mixtures are run in parallel with different agent concentrations to obtain a different response to the various concentrations. Typically, one of these concentrations serves as a negative control, i.e., at zero concentration of agent or at a concentration of agent below the limits of assay detection.

Candidate agents useful in accordance with the invention encompass numerous chemical classes, although typically they are organic compounds. Preferably, the candidate pharmacological agents are small organic compounds, i.e., those having a molecular weight of more than 50 yet less than about 2500, preferably less than about 1000 and, more preferably, less than about 500. Candidate agents comprise functional chemical groups necessary for structural interactions with proteins and/or nucleic acid molecules, and typically include at least an amine, carbonyl, hydroxyl or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as peptides, saccharides, fatty acids, sterols, isoprenoids, purines, pyrimidines, derivatives or structural analogs of the above, or combinations thereof and the like. Where the agent is a nucleic acid molecule, the agent typically is a DNA or RNA molecule, although modified nucleic acid molecules as defined herein are also contemplated.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily be modified through conventional chemical, physical, and biochemical means. Further, known pharmacological agents may be subjected to directed or random chemical modifications such as acylation, alkylation, esterification, amidification, etc. to produce structural analogs of the agents.

A variety of other reagents also can be included in the mixture. These include reagents such as salts, buffers, neutral proteins (e.g., albumin), detergents, etc. which may be used to facilitate optimal protein-protein and/or protein-nucleic acid binding. Such a reagent may also reduce non-specific or background interactions of the reaction components. Other reagents that improve the efficiency of the assay such as protease inhibitors, nuclease inhibitors, antimicrobial agents, and the like may also be used.

Other active agents can be tested and dosing can be optimized using animal models of IBD. Several animal models of the disease state. For instance an animal model is described in detail in the Examples. In this approach, various irritants, such as ethanol, acetic acid, formalin, immune complexes, trinitrobenzene sulphonic acid (TNBS), bacterial products or carrageenan are used to generate acute or chronic inflammation. A model of this kind has been developed by Wallace, J. and coworkers [Morris et al., Gastroenterology 96, 795 (1989)]. Another type of animal model of IBD includes animals spontaneously developing diseases reminiscent of some forms of IBD. Spontaneous animal models include C3H/HeJ mouse, Japanese waltzing mice, swine dysentery and equine colitis, caused by *C. difficile*, and the cotton top tamarin. A third approach involves the use of transgenic animals to model IBD. Most human patients who have ankylosing spondylitis also carry the gene for HLA-B27. It has been observed that such patients are at greater risk of developing IBD. HLA-B27 transgenic rats, which were attempted to model spondyloarthropathies, in addition to the joint disease, also showed symptoms of chronic inflammation of the bowel which, though not identical, had many similarities with the disease. Another suitable transgenic animal model is based on IL-10 "knockout" mice. IL-10 is produced by TH2 cells, stimulates B cells to produce antibody, downregulates macrophages reducing the production of IL-1, IL-6, IL-8 and TNF-α, and shifts the balance of antigen presentation from macrophages to B cells.

The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours.

The practice of the present invention will employ, unless otherwise indicated, conventional methods of chemistry, biochemistry, molecular biology, cell biology, genetics, immunology and pharmacology, within the skill of the art. Such techniques are explained fully in the literature. See, e.g., Gennaro, A. R., ed. (1990) *Remington's Pharmaceutical Sciences*, 18$^{th}$ ed., Mack Publishing Co.; Hardman, J. G., Limbird, L. E., and Gilman, A. G., eds. (2001) *The Pharmacological Basis of Therapeutics*, 10$^{th}$ ed., McGraw-Hill Co.; Colowick, S. et al., eds., *Methods In Enzymology*, Academic Press, Inc.; Weir, D. M., and Blackwell, C. C., eds. (1986) *Handbook of Experimental Immunology*, Vols. I-IV, Blackwell Scientific Publications; Maniatis, T. et al., eds. (1989) *Molecular Cloning: A Laboratory Manual*, 2$^{nd}$ edition, Vols. I-III, Cold Spring Harbor Laboratory Press; Ausubel, F. M. et al., eds. (1999) *Short Protocols in Molecular Biology*, 4$^{th}$ edition, John Wiley & Sons; Ream et al., eds. (1998) *Molecular Biology Techniques: An Intensive Laboratory Course*, Academic Press; Newton, C. R., and Graham, A., eds. (1997) *PCR* (Introduction to Biotechniques Series), 2$^{nd}$ ed., Springer Verlag.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference. Nothing herein is to be construed as an admission that the invention is not entitled to antedate any art described herein by virtue of prior invention.

EXAMPLES

Example 1

Experimental Animal Models of Inflammatory Bowel Disease

The effectiveness of compounds and methods of the present invention on intestinal barrier protection and treatment of inflammatory bowel disease (IBD) in TNBS (2,4,6-trinitrobenzene sulfonic acid)-induced colitis, an established animal model of inflammatory bowel disease, was examined. TNBS-induced colitis was induced in mice using a modification of techniques previously described. (See Morris et al (1989) Gastroenterology 96:795-803; Boirivant et al (1998) J Exp Med 188:1929-1939; Karhausen et al (2004) J Clin Invest 114:1098-1106.)

Mice were shaved on the abdomen (causing total depletion of hair and microlesions) and were then sensitized to subsequent treatment by epicutaneous application of 1% TNBS (Sigma-Aldrich) in 100% ethanol on day minus 7. Seven days later, on day 0, animals were sedated with a 2.5% Tribromo-ethanol solution in phosphate-buffered saline (14 µl/g body weight), followed by intrarectal administration of a 2.5% TNBS solution in 50% ethanol (5 µl/g body weight). Administration of the 2.5% TNBS solution was carried out using an epidural catheter (FlexTip Plus Epidural Catheter, Arrow International), which was inserted approximately 6 cm ab ano followed by release of the TNBS solution. To ensure the continuance of the TNBS solution in the colon, mice were suspended in a vertical position for at least 5 minutes following administration. Vehicle control animals received a corresponding volume of 50% ethanol solution alone.

Unless otherwise indicated, compounds of the invention were administered to animals intraperitoneally (i.p.) as a solution. Animals were dosed with compound (40 mg/kg/day or 20 mg/kg/day) on day minus 1, day 0, and day 1, or exclusively on day 0 and day 1, by i.p. injection. On day 0, TNBS treatment was performed on animals 4 hours after injection of compound.

Example 2

Intestinal Permeability

The effect of compounds of the present invention on intestinal permeability and intestinal barrier function was examined using an established animal model of inflammatory bowel disease (described above in Example 1). Intestinal permeability, a measure of intestinal barrier function, was examined using two intestinal permeability tracers: FITC-labeled-dextran and Texas Red-labeled lipopolysaccharide (LPS).

Intestinal permeability (a measure of intestinal barrier protection and intestinal barrier function) was examined using a FITC-labeled-dextran method as described previously. (See, e.g., Furuta et al (2001) J Exp Med 193:1027-1034 and Napolitano et al (1996) Shock 5:202-207.) Briefly, TNBS-colitis was induced in mice as described above in Example 1. Following induction of TNBS-colitis, mice were administered Compound A (60 mg/kg, i.p.; designated C in FIG. 1A) or PBS (vehicle control; designated V in FIG. 1A). After 20 hours, animals were gavaged with 0.6 mg/g body weight of FITC-dextran (prepared at a concentration of 120 mg/ml; Sigma-Aldrich) (n=3-5 per condition). Four hours later, changes in intestinal permeability were determined by measurement of serum FITC-dextran levels.

As shown in FIG. 1A, TNBS-colitis animals administered Compound A had lower levels of serum FITC-dextran compared to those in vehicle control animals. (Data in FIG. 1A are expressed as mean serum FITC-dextran levels+/− SD (relative to that measured in vehicle control animals) from data pooled from 4 animals for each experimental condition.) In this animal model, serum levels of FITC-dextran are an indicator of the extent of intestinal permeability and intestinal barrier function. These results, therefore, indicated that administration of Compound A to animals with colitis reduced intestinal permeability.

Intestinal permeability was also examined using Texas Red labeled LPS. Briefly, TNBS-colitis was induced in mice as described above in Example 1. Following induction of TNBS-colitis, mice were administered Compound A (60 mg/kg, i.p.; designated C in FIG. 1B) or PBS (vehicle control; designated V in FIG. 1B). After 20 hours, animals were gavaged with 0.0125 mg/g body weight of Texas Red labeled *E. coli* LPS (prepared at a concentration of 2.5 mg/ml; Sigma-Aldrich). Four hours later, changes in intestinal permeability were determined by measurement of serum Texas Red labeled LPS levels.

As shown in FIG. 1B, TNBS-colitis animals administered Compound A had lower levels of serum Texas Red labeled LPS compared to that in vehicle control animals. (Data in FIG. 1B are expressed as mean serum Texas Red labeled LPS levels+/−SD (relative to that measured in vehicle control animals) from data pooled from 3-5 animals for each experimental condition.) In this animal model, serum levels of Texas Red labeled LPS are an indicator of the extent of intestinal permeability and intestinal barrier function. These results, therefore, indicated that administration of Compound A to animals with colitis reduced intestinal permeability.

These results showed that methods and compounds of the present invention reduced intestinal permeability in an animal model of IBD. These results further suggested that methods and compounds of the present invention are effective at preserving, maintaining, or enhancing and improving intestinal barrier function of the intestine in IBD.

Example 3

Weight Loss

The effect of methods and compounds of the present invention on weight loss associated with inflammatory bowel disease was studied using an established animal model of colitis (described above in Example 1). Monitoring weight loss is a reliable method to assess TNBS-colitis severity in this animal model, as previously described. (See Neurath et al (2000) Int Rev Immunol 19:51-62.)

Animals were administered Compound A (20 mg/kg or 40 mg/kg, i.p.) or vehicle control on day minus 1, day 0, and day 1. TNBS-colitis was induced in mice on day 0, as described above in Example 1. Body weight of the mice was monitored following induction of TNBS-colitis. Only those animals that showed an initial 5% loss in body weight after induction of TNBS-colitis were included in subsequent weight loss analyses. Animal body weight was monitored each day for 3 days.

Figure 2:
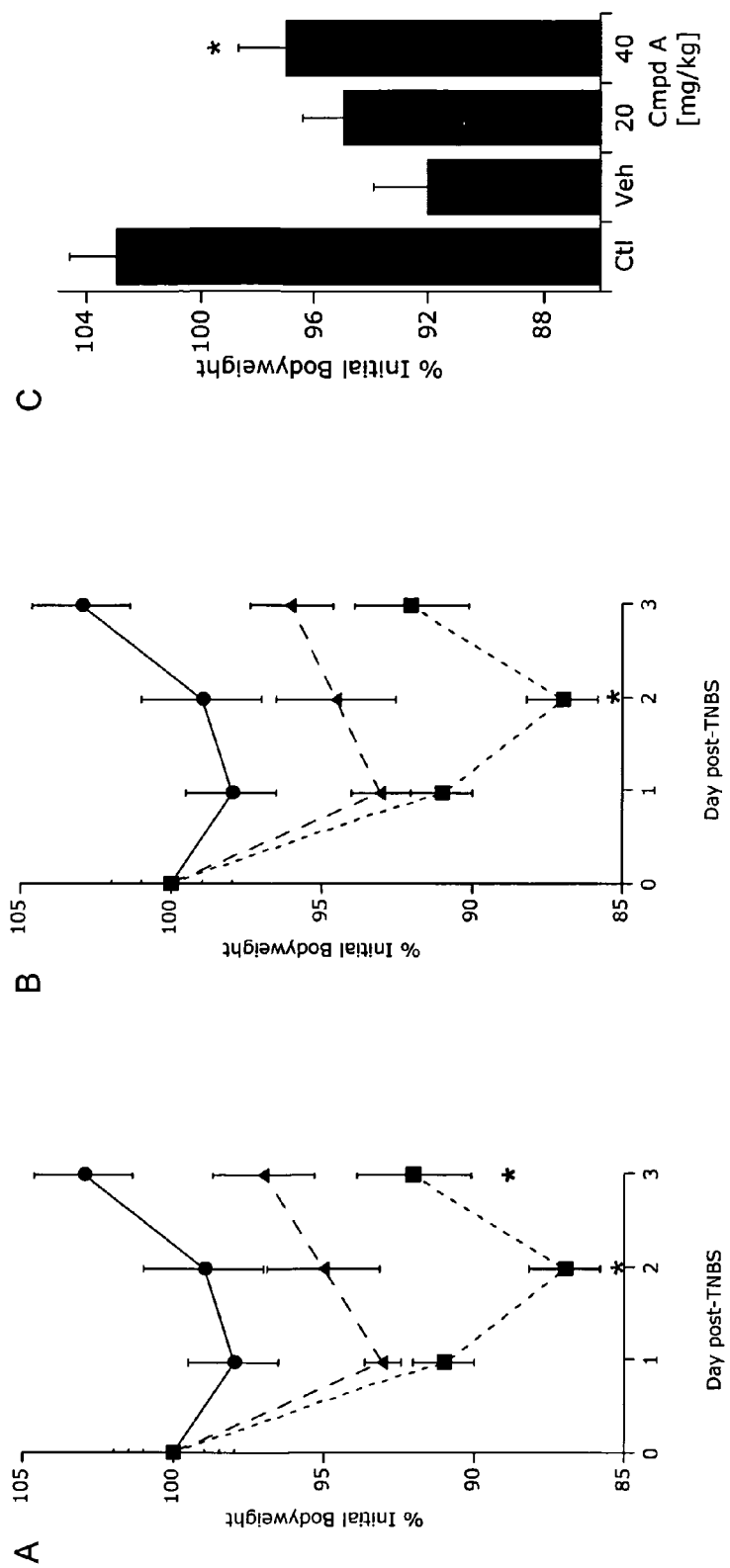
FIGS. 2A, 2B, and 2C set forth data showing methods and compounds of the present invention prevented weight loss and improved weight gain in an animal model of inflammatory bowel disease.

Control (healthy non-TNBS-colitis) animals (closed circles in FIGS. 2A and 2B) showed an increase in body weight at day 3 in this study compared to that in non-treated TNBS-colitis animals. (See FIGS. 2A, 2B, and 2C.) As shown in FIGS. 2A and 2B, administration of Compound A (40 mg/kg, closed triangles in FIG. 2A; 20 mg/kg, closed triangles in FIG. 2B) to TNBS-colitis animals on day minus 1, day 0, and day 1 resulted in a reduction in the extent of initial body weight loss compared to the initial body weight loss in vehicle-control treated TNBS-colitis animals (closed squares in FIGS. 2A and 2B). Additionally, TNBS-colitis animals administered Compound A showed a greater increase in body weight gain (i.e., greater recovery from weight loss) by day 3 compared to the increase in body weight gain observed in vehicle/control-treated TNBS-colitis animals. (See FIGS. 2A and 2B.)

FIG. 2C shows results from changes in body weight summarized from measurements obtained on day 3 for each of the experimental conditions described above. Data in FIG. 2C are presented as percent change in initial body weight+/−SD using body weight measurements obtained from 4-6 animals for each experimental condition. As shown in FIG. 2C, healthy non-TBNS-colitis control (Ctl) animals showed an increase in body weight at day 3 in this study. Vehicle-treated TNBS-colitis (Veh) animals had an average body weight of approximately 92% of their initial body weight at day 3 following the induction of TNBS-colitis. TNBS-colitis animals administered either 20 mg/kg or 40 mg/kg Compound A, however, had an average body weight of approximately 95% and 97%, respectively, at day 3 following the induction of TNBS-colitis. These results showed that administration of Compound A provided therapeutic benefit by reducing the weight loss associated with TNBS-colitis. As weight loss is a reliable method to assess disease severity in this animal model of IBD, these data indicated that Compound A was effective at reducing the severity of the disease. Taken together, these results showed that compounds and methods of the present invention are effective at reducing the severity of inflammatory bowel disease.

Example 4

Colon Length

The effect of methods and compounds of the present invention on changes in colon length (i.e., colon length shortening) associated with inflammatory bowel disease was studied using an established animal model of inflammatory bowel disease (described above in Example 1). In this animal model, a change (i.e., shortening) in colon length is a marker of the severity of IBD. (See Karhausen et al (2004) J Clin Invest 114:1098-1106.)

Animals were administered Compound A (20 mg/kg or 40 mg/kg, i.p.) or vehicle control on day minus 1, day 0, and day 1. TNBS-colitis was induced in mice on day 0, as described above in Example 1. Colon length was determined by measurement of the distance from the most distal aspect of the cecum to the most terminal aspect of the rectum on day 3 post-induction of TNBS-colitis.

Figure 3:
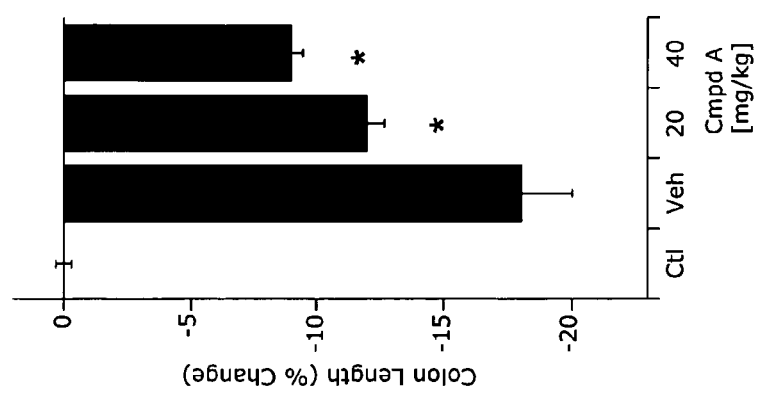
FIG. 3 sets forth data showing methods and compounds of the present invention reduced colon length shortening in an animal model of inflammatory bowel disease.

FIG. 3 shows changes in colon length from measurements obtained on day 3 for each of the experimental conditions. Data in FIG. 3 are presented as percent change in colon length (+/−SD) using colon length measurements obtained from 4-6 animals from each experimental condition. As shown in FIG. 3, vehicle-treated TNBS-colitis (Veh) animals had an average decrease in colon length of greater than 17% compared to colon length in healthy non-TBNS-colitis control (Ctl) animals at day 3 in this study. TNBS-animals administered either 20 mg/kg or 40 mg/kg Compound A, however, had an average decrease in colon length of approximately 12% and 8%, respectively, at day 3 following the induction of TNBS-colitis.

These results showed that administration of Compound A reduced colon length shortening associated with TNBS-colitis. As the extent of colon shortening is indicative of the severity of disease activity and a reliable method to assess TNBS-colitis severity in this animal model, this data indicated that Compound A was effective at reducing the severity of the disease. Taken together, these results showed that compounds and methods of the present invention are effective at reducing the severity of inflammatory bowel disease and at providing an effective treatment for inflammatory bowel disease.

Example 5

Histological Analysis

The effect of methods and compounds of the present invention on structural changes of the colon associated with inflammatory bowel disease was studied using an established animal model of inflammatory bowel disease (described above in Example 1). Animals were administered Compound A (40 mg/kg, i.p.) or vehicle control on day minus 1, day 0, and day 1. TNBS-colitis was induced in mice on day 0, as described above in Example 1. On day three post induction of TNBS-colitis, colon sections from the mice were obtained and prepared for histological analysis.

Figure 4:
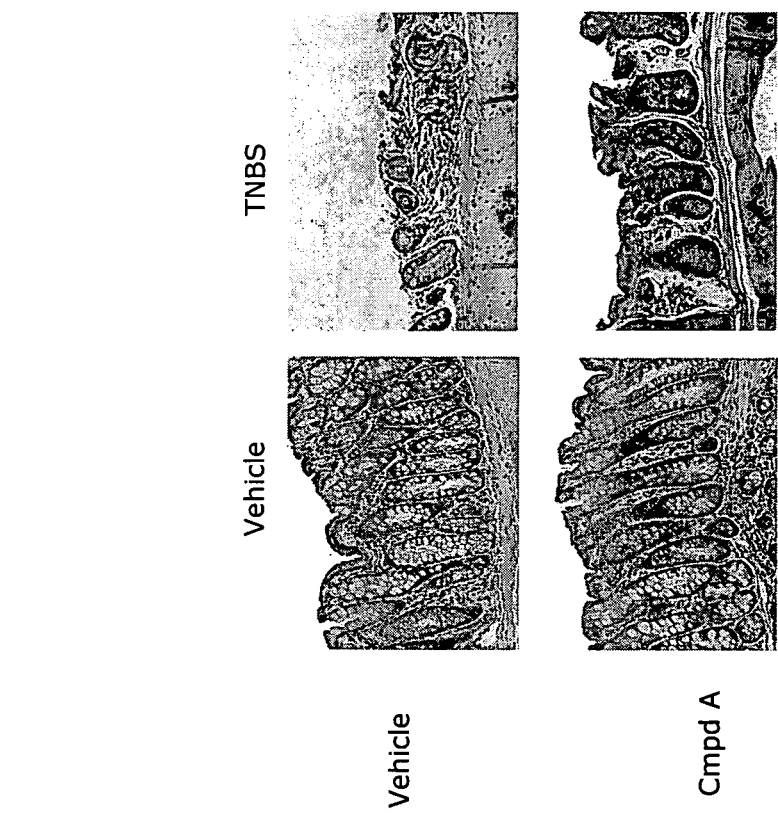
FIG. 4 shows methods and compounds of the present invention improved intestinal tissue architecture in an animal model of inflammatory bowel disease.

As shown in FIG. 4, histological examination of colon sections obtained from vehicle-control TNBS-colitis animals (Vehicle/TNBS) showed tissue thickening, villous blunting, and an overall loss of organized tissue architecture compared to that observed in colon sections obtained from healthy non-TBNS-colitis control animals (Vehicle/Vehicle). By contrast, colon sections obtained from TNBS-colitis animals administered 40 mg/kg Compound A (Cmpd A/TNBS) showed a reduction in inflammatory infiltrate, a reduction in villous blunting, and an overall general preservation of tissue architecture compared to vehicle-control treated TNBS-colitis animals. (See FIG. 4.)

These results showed that methods and compounds of the present invention were effective at treating IBD, as evidenced by a reduction in IBD-associated inflammatory infiltrate and villous blunting following administration of compound of the present invention.

Example 6

TNFα Expression

The effect of methods and compounds of the present invention on expression of the inflammatory cytokine tumor necrosis factor-alpha (TNFα) associated with inflammatory bowel disease was studied using an established animal model of colitis (described above in Example 1). Expression of the inflammatory cytokine TNFα has been shown to correlate with the severity of TNBS-induced colitis. (See Neurath et al (1997) Eur J Immunol 27:1743-1750.), and various current treatments for IBD target TNFα, such as, for example, infliximab and adalimumab.

Animals were administered Compound A (20 mg/kg or 40 mg/kg, i.p.) or vehicle control on day minus 1, day 0, and day 1. TNBS-colitis was induced in mice on day 0, as described above in Example 1. On day three post TNBS-induction of colitis, colonic mucosal scrapings (enriched in epithelial cells) were obtained from the mice and stored in RNAlater (Ambion), as described previously. (Karhausen et al (2004) J Clin Invest 114:1098-1106.) In these studies, mRNA obtained from epithelial-enriched colonic scrapings was used to perform real-time PCR analysis for TNFα expression as follows. Colonic mucosal scrapings were incubated for 30 minutes in TRIzol® (Invitrogen, Carlsbad, Calif.) and subsequently homogenized using a 22-gauge needle (Becton Dickinson). RNA was isolated by phenol-chloroform extraction. Reverse-transcription was done using Sprint PowerScript Double Pre-Primed Single Shots (ClonTech, Mountain View, Calif.). Amplification was performed on an i-Cycler IQ real-time PCR detection system (BioRad Laboratories, Hercules, Calif.) using the following gene-specific primers: TNFα; forward primer 5'-CCA CCA CGC TCT TCT GTC TAC-3', (SEQ ID NO. 1) reverse primer 5'-TGG GCT ACA GGC TTG TCA CT-3'(SEQ ID NO. 2); β-Actin, forward primer 5'-CTA GGC ACC AGG GTG TGA T-3'(SEQ ID NO. 3), reverse primer 5'-TGC CAG ATC TTC TCC ATG TC-3'(SEQ ID NO. 4).

Amplification cSycle parameters were as follows: 3 minutes at 95° C.; 40 cycles of 45 seconds at 95° C., 30 seconds at 58° C., 30 seconds at 72° C.; followed by repetitive melting cycles to establish amplification product specificity. Comparison of gene expression in a semi-quantitative manner was performed based on the mathematical model of Pfaffl. (Pfaffl (2001) Nucleic Acids Res 29:e45.)

Figure 5:
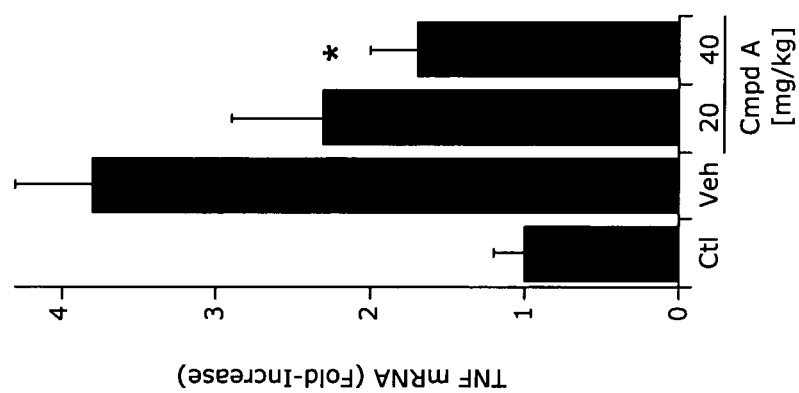
FIG. 5 sets forth data showing methods and compounds of the present invention reduced tumor necrosis factor-alpha in colon epithelial cells in an animal model of inflammatory bowel disease.

As shown in FIG. 5, mice subjected to TNBS-induced colitis showed a 3.8±0.4 fold increase in TNFα mRNA levels compared to that observed in healthy non-TNBS-colitis control animals. TNBS-colitis mice administered 40 mg/kg Compound A on day minus 1, day 0, and day 1 showed a significant decrease (*$p<0.01$) in TNFα mRNA levels compared to that observed in non-treated TNBS-colitis mice. (See FIG. 5.) These results showed that methods and compounds of the present invention are effective at reducing TNFα mRNA levels associated with inflammatory bowel disease.

Example 7

PHD Expression

HIF Prolyl Hydroxylase (PHD) expression in human epithelia and colonic tissue was examined. In particular the expression patterns of HIF PHD isoforms in human colonic epithelia and in tissues derived from healthy adults and patients with ulcerative colitis or Crohn's disease were examined.

Figure 6:
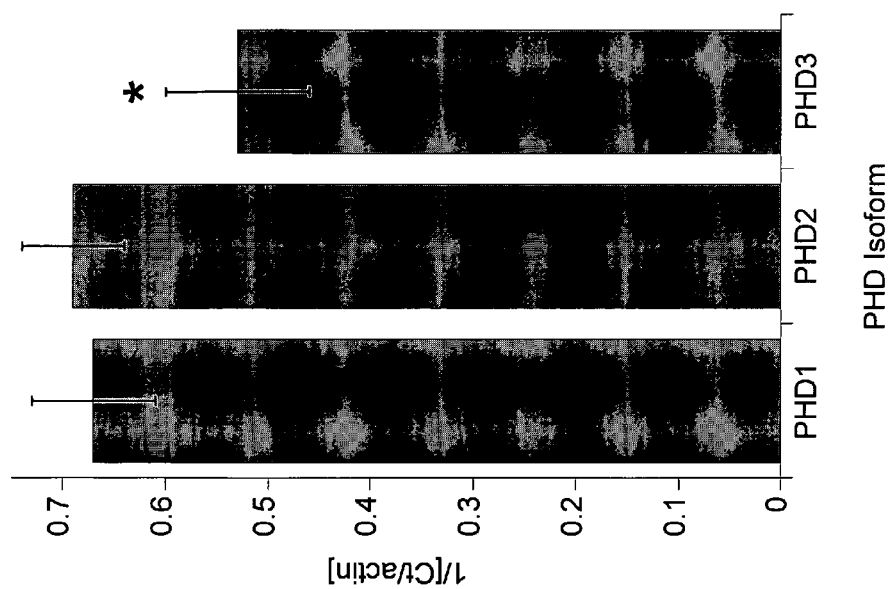
FIG. 6 is a bar graph showing an analysis of PHD isoforms in human colonic epithelial cells. Messenger RNA derived from colonic epithelial cell line (Caco2 cells) were screened for expression of the various isoforms by real-time PCR. PHD3 levels were significantly lower than either PHD1 or PHD2 ($p<0.001$, $n=33$ per group).

Initially, the expression of PHD isoforms was screened in human colonic epithelia. As shown in FIG. 6, mRNA derived from colonic epithelial cell line (Caco2 cells) were screened for expression of the various isoforms by real-time PCR. The pattern of expression was PHD1≥PHD2>>>PHD3, with PHD3 levels significantly lower than either PHD1 or PHD2 ($p<0.001$, n=33).

Figure 7:
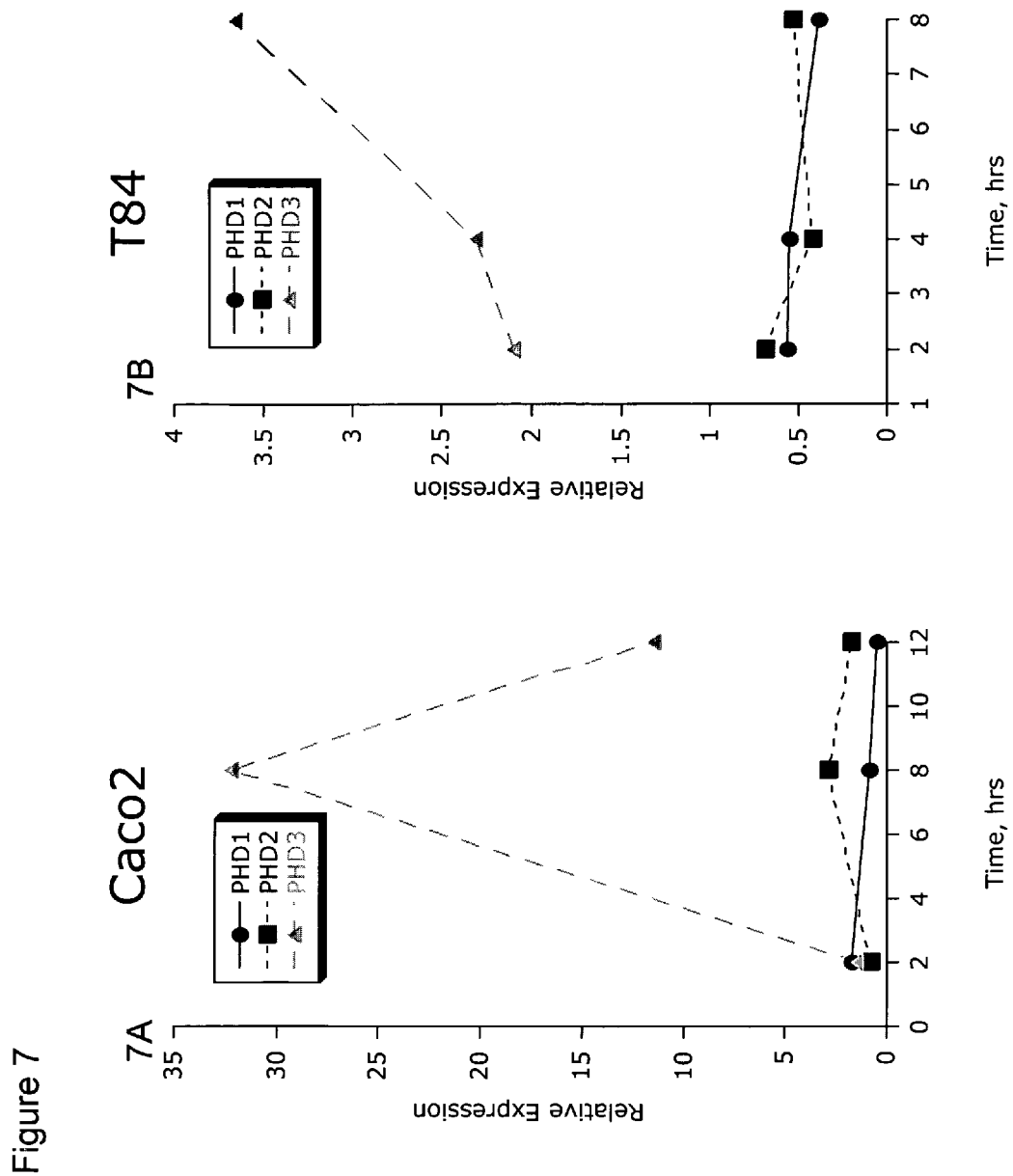
FIG. 7 is two graphs depicting analysis of PHD isoforms in human colonic epithelial cells in response to hypoxia. Colonic epithelial cell lines Caco2 (7A) and T84 (7B) cells were subjected to normoxia or hypoxia (pO2 20 torr for 2, 4, 8 or 12 hr). Cells were harvested and isolated mRNA analyzed for expression PHD-1, -2 and -3 isoforms by real-time PCR.

In FIG. 7, colonic epithelial cell lines (Caco2 and T84 cells) were subjected to normoxia or hypoxia (2, 4, 8 or 12 hr), cells were harvested and mRNA analyzed for expression of all three PHD isoforms by real-time PCR. As can be seen, the relative mRNA expression PHD-1 and PHD-2 did not significantly change, while PHD-3 levels increased significantly with time in hypoxia.

Figure 8:
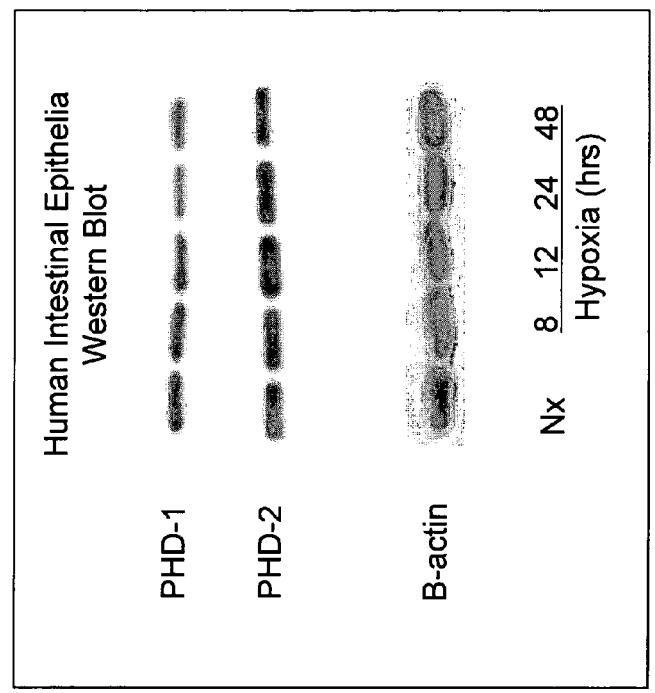
FIG. 8 depicts a Western blot protein analysis of PHD isoforms in human colonic epithelial cells in response to hypoxia. Protein analysis (western blotting) of PHD-1 and PHD-2 in Caco2 cells subjected to hypoxia (pO2 20 torr for 8, 12, 24 or 48 hr). The pattern of expression revealed a loss of both PHD-1 and PHD-2 with increasing periods of hypoxia, relative to beta-actin controls.

FIG. 8 shows protein analysis (western blotting) of PHD-1 and PHD-2 with hypoxia. The pattern of expression revealed a loss of both PHD-1 and PHD-2 with increasing periods of hypoxia.

Figure 9:
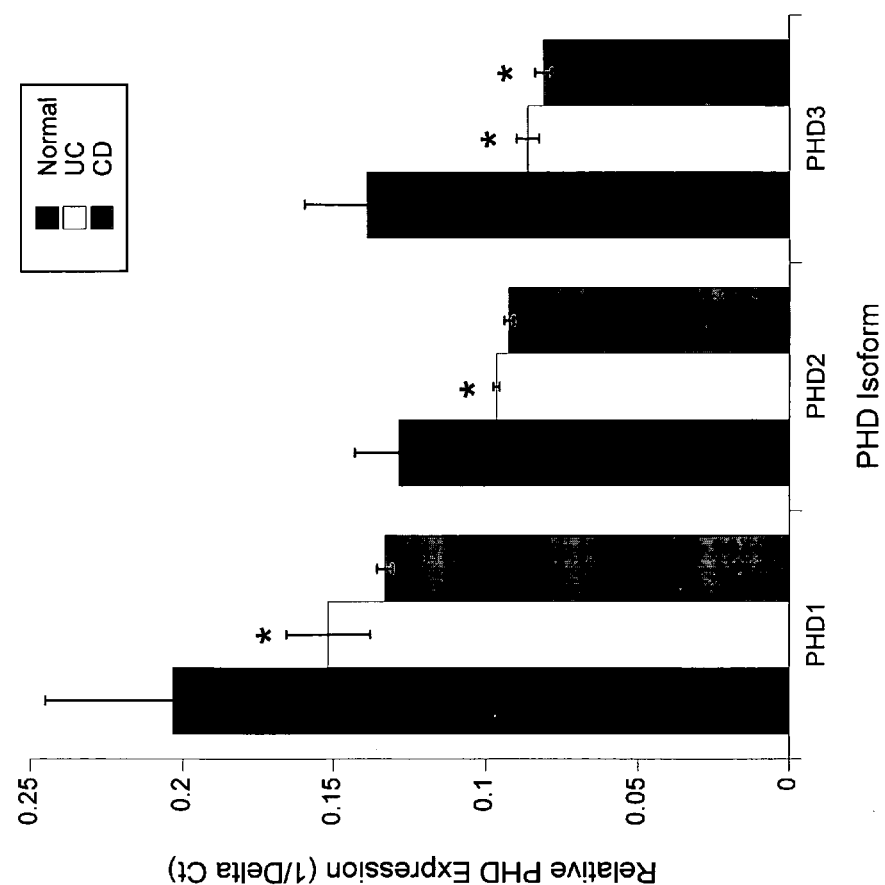
FIG. 9 is a bar graph depicting analysis of PHD isoforms in healthy and diseased colonic biopsies. mRNA expression analysis for PHD-1, PHD-2 and PHD-3 in samples derived from healthy ($n=12$), ulcerative colitis (UC, $n=22$) and Crohn's disease (CD, $n=18$) colonic biopsies. All PHD mRNA levels were decreased in diseased colonic biopsies, with significant differences noted for PHD-1, PHD-2 and PHD-3 in ulcerative colitis (where * indicates $p<0.05$) and for PHD-3 in Crohns disease (where * indicates $p<0.05$).

FIG. 9 shows mRNA expression analysis for PHD-1, PHD-2 and PHD-3 in samples derived from healthy (n=12), ulcerative colitis (UC, n=22) and Crohn's disease (CD, n=18) colonic biopsies. All PHD mRNA levels were decreased in diseased colonic biopsies, with significant differences noted for PHD-1, PHD-2 and PHD-3 in ulcerative colitis ($p<0.05$) and for PHD-3 in Crohns' disease ($p<0.05$).

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

I claim:

1. A method for treating inflammatory bowel disease in a subject having or at risk of having inflammatory bowel disease, comprising
administering a therapeutically effective amount of an agent that inhibits HIF hydroxylase to the subject.

2. The method of claim 1, wherein the inflammatory bowel disease is ulcerative colitis.

3. The method of claim 1, wherein the inflammatory bowel disease is Crohn's disease.

4. The method of claim 1, wherein the agent that inhibits HIF hydroxylase is a HIF prolyl hydroxylase inhibitor.

5. The method of claim 4, wherein the HIF prolyl hydroxylase is EGLN1, EGLN2, or EGLN3.

6. The method of claim 1, wherein the agent that inhibits HIF hydroxylase is a HIF asparaginyl hydroxylase inhibitor.

7. The method of claim 6, wherein the HIF asparaginyl hydroxylase is FIH.

8. The method of claim 1, wherein the agent that inhibits HIF hydroxylase is a compound that inhibits 2-oxoglutarate dioxygenase enzyme activity.

9. The method of claim 1, wherein the agent that inhibits HIF hydroxylase is [(4-Hydroxy-7-phenylsulfanyl-isoquinoline-3-carbonyl)-amino]-acetic acid.

10. The method of claim 1, wherein the agent that inhibits HIF hydroxylase is a HIF hydroxylase expression inhibitor.

11. The method of claim 10 wherein the HIF hydroxylase expression inhibitor is small interfering nucleic acid.

12. The method of claim 10, wherein the HIF hydroxylase expression inhibitor is a transgene that expresses a small interfering nucleic acid capable of inhibiting expression of a HIF hydroxylase gene.

13. The method of claim 1, wherein the agent that inhibits HIF hydroxylase selectively inhibits PHD-1.

14. The method of claim 1, wherein the agent that inhibits HIF hydroxylase selectively inhibits PHD-2.

15. The method of claim 1, wherein the agent that inhibits HIF hydroxylase selectively inhibits PHD-3.

16. A method for reducing or ameliorating a symptom of inflammatory bowel disease in a subject, the method comprising administering a therapeutically effective amount of an agent that inhibits HIF hydroxylase to the subject.

17. The method of claim 16, wherein the subject has ulcerative colitis.

18. The method of claim 16, wherein the subject has Crohn's disease.

19. A method for reducing intestinal permeability in a subject having inflammatory bowel disease, the method comprising administering a therapeutically effective amount of an agent that inhibits HIF hydroxylase to the subject.

20. A method for improving intestinal barrier function in a subject having inflammatory bowel disease, the method comprising administering a therapeutically effective amount of an agent that inhibits HIF hydroxylase to the subject.

* * * * *

UNITED STATES PATENT AND TRADEMARK OFFICE
CERTIFICATE OF CORRECTION

| | | |
|---|---|---|
| PATENT NO. | : 8,962,530 B2 | Page 1 of 1 |
| APPLICATION NO. | : 12/666438 | |
| DATED | : February 24, 2015 | |
| INVENTOR(S) | : Sean P. Colgan | |

It is certified that error appears in the above-identified patent and that said Letters Patent is hereby corrected as shown below:

In the Specification

At Column 1, add the following "Related Applications" section, after the title:

--<u>Related Applications</u>

This application is a national stage filing under 35 U.S.C. § 371 of international application PCT/US08/07962, filed June 26, 2008, which claims the benefit of U.S. Provisional Application No. 60/946,537, filed on June 27, 2007. The entire content of each of the prior applications is incorporated by reference herein in its entirety.--

Signed and Sealed this
Thirtieth Day of June, 2015

Michelle K. Lee
*Director of the United States Patent and Trademark Office*